US006586402B1

(12) United States Patent
Delansorne et al.

(10) Patent No.: US 6,586,402 B1
(45) Date of Patent: Jul. 1, 2003

(54) LH-RH PEPTIDE ANALOGUES, THEIR USES AND PHARMACEUTICAL COMPOSITIONS CONTAINING THEM

(75) Inventors: Rémi Delansorne, Nice (FR); Jacques Paris, Nice (FR)

(73) Assignee: Laboratoire Theramex, Albert (MC)

( * ) Notice: Subject to any disclaimer, the term of this patent is extended or adjusted under 35 U.S.C. 154(b) by 0 days.

(21) Appl. No.: 09/450,443

(22) Filed: Nov. 30, 1999

Related U.S. Application Data

(63) Continuation of application No. PCT/EP98/02802, filed on May 6, 1998.

(30) Foreign Application Priority Data

Jun. 2, 1997 (EP) .......................................... 97 401 212

(51) Int. Cl.$^7$ ........................... A61K 38/09; C07K 7/23

(52) U.S. Cl. ............................. 514/15; 514/13; 514/16; 530/323

(58) Field of Search .............................. 514/15, 16, 13; 530/332; 930/130

(56) References Cited

U.S. PATENT DOCUMENTS 5,140,009 A * 8/1992 Haviv et al. .................. 514/16

6,153,587 A * 11/2000 Delansorne et al. .......... 514/15

FOREIGN PATENT DOCUMENTS

EP A 0 413209 A1 * 8/1991

OTHER PUBLICATIONS

Curti, Crittical Review in Oncology/Hematology, vol. 14, pp. 14–29, 1993.*

Ross et al., Immunology Today, vol. 11, No. 6, 1990.*

Siemen in Rodent Tumor Models in Exaperimental Cancer Therapy, edited by Robert F. Kallman, published by Pregamon Press, 1987, pp. 12–15.*

Trott in Rodent Tumor Models in Exaperimental Cancer Therapy, edited by Robert F. Kallman, published by Pregamon Press, 1987, pp. 6–11.*

Jaine Sci. Amer. vol. 271, pp. 58–65, Jul. 1994.*

* cited by examiner

*Primary Examiner*—Christopher S. F. Low
*Assistant Examiner*—Abdel A. Mohamed
(74) *Attorney, Agent, or Firm*—Dennison, Schultz & Dougherty

(57) ABSTRACT

The invention relates to LH-RH peptide analogues with excellent affinity for LH-RH receptors, of the formula:

A1-A2-A3-A4-A5-A6-HAA-A7-Pro-Z (I)

Figure 1:
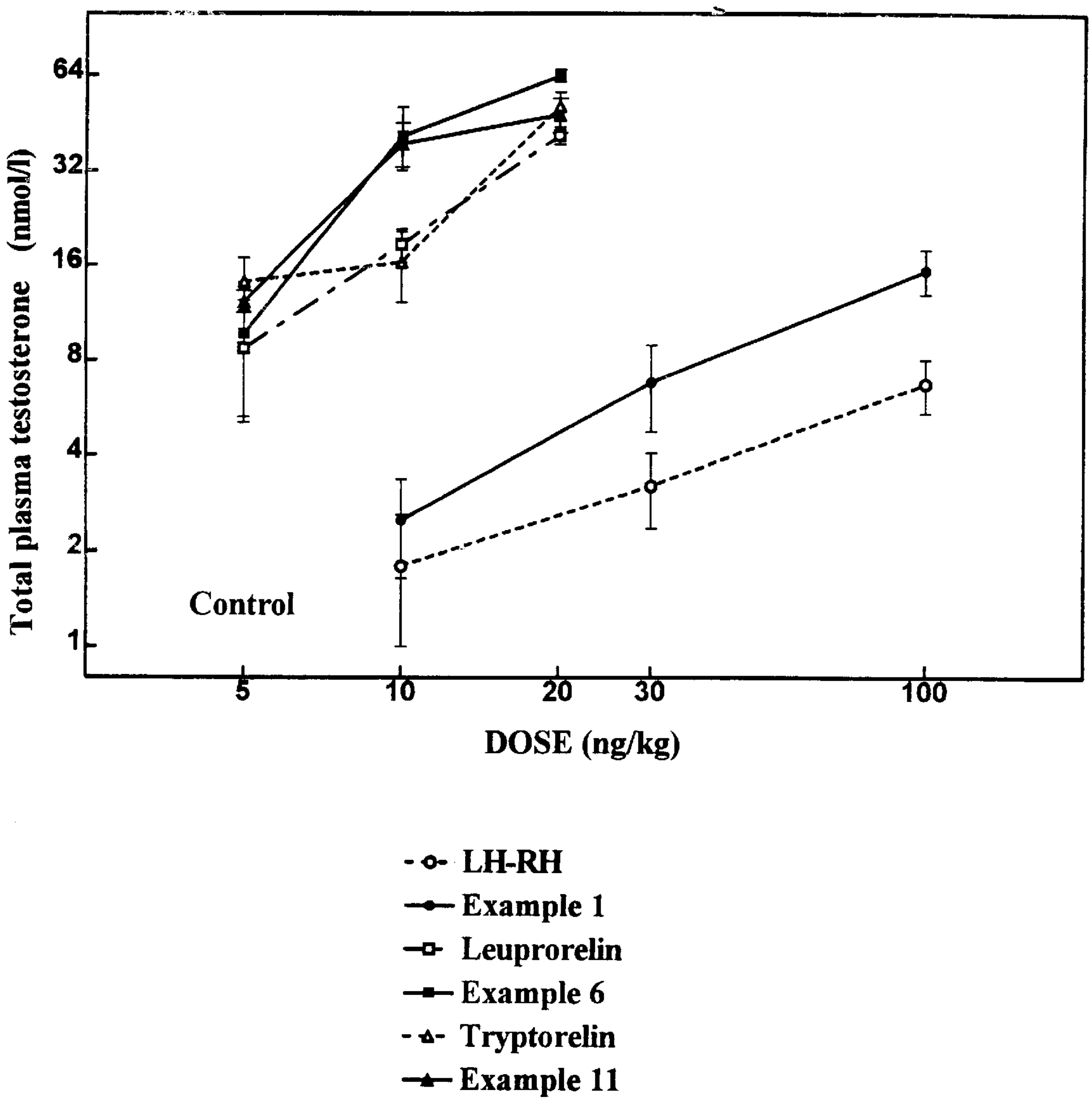

The invention also relates to the uses of said peptide analogues and to the pharmaceutical compositions containing them.

22 Claims, 1 Drawing Sheet

SEQUENCE LISTING

```
<160> NUMBER OF SEQ ID NOS: 39

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: LH-RH
      analogue
<220> FEATURE:
<221> NAME/KEY: SITE
<222> LOCATION: (1)
<223> OTHER INFORMATION: Xaa is pGlu; D-pGlu; Sar; AcSar; Pro; AcPro;
      ForPro; OH-Pro; Ac- OH-Pro; dehydro-Pro; Ac-dehydro-Pro; Ser;
      D-Ser; Ac-D-Ser; Thr; D-Thr; Ac-D-Thr; or an aromatic D-amino acid
<220> FEATURE:
<221> NAME/KEY: SITE
<222> LOCATION: (2)
<223> OTHER INFORMATION: Xaa is His ; or an aromatic D-amino acid
<220> FEATURE:
<221> NAME/KEY: SITE
<222> LOCATION: (3)
<223> OTHER INFORMATION: Xaa is an aromatic L- or D-amino acid
<220> FEATURE:
<221> NAME/KEY: SITE
<222> LOCATION: (4)
<223> OTHER INFORMATION: Xaa is Ala, Ser, D-Ser, MeSer, Ser(OBut),
      Ser(OBzl) or Thr
```

-continued

```
<220> FEATURE:
<221> NAME/KEY: SITE
<222> LOCATION: (5)
<223> OTHER INFORMATION: Xaa is an aromatic L-amino acid or a basic L-
      or D-amino acid
<220> FEATURE:
<221> NAME/KEY: SITE
<222> LOCATION: (6)
<223> OTHER INFORMATION: Xaa is Gly; D-Pro; D-Ser; D-Thr; D-Cys; D-Met;
      D-Pen; D-(S-Me)Pen; D-(S-Et)Pen; D-Ser(OBut); D-Asp(OBut);
      D-Glu(OBut); D-Thr(OBut);D- Cys(OBut); an aza-amino acid; D-His
<220> FEATURE:
<221> NAME/KEY: SITE
<222> LOCATION: (6)
<223> OTHER INFORMATION: Xaa is an aliphatic D-amino acid with a
      (C1-C8)alkyl or a (C3-C6)cycloalkyl side chain; an aromatic
      D-amino acid; D-cyclohexadienyl- Gly; D-perhydronaphthyl-Ala
<220> FEATURE:
<221> NAME/KEY: SITE
<222> LOCATION: (6)
<223> OTHER INFORMATION: Xaa is D-perhydrodiphenyl-Ala; or a basic L- or
      D-amino acid
<220> FEATURE:
<221> NAME/KEY: SITE
<222> LOCATION: (7)
<223> OTHER INFORMATION: Xaa is Npg or adamantyl-Ala
<220> FEATURE:
<221> NAME/KEY: SITE
<222> LOCATION: (8)
<223> OTHER INFORMATION: Xaa is a basic L- or D-amino acid
<220> FEATURE:
<221> NAME/KEY: SITE
<222> LOCATION: (10)
<223> OTHER INFORMATION: Xaa is Gly; D-Ala or azaGly

<400> SEQUENCE: 1

Xaa Xaa Xaa Xaa Xaa Xaa Xaa Xaa Pro Xaa
  1               5                  10


<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: LH-RH
      analogue
<220> FEATURE:
<221> NAME/KEY: SITE
<222> LOCATION: (1)
<223> OTHER INFORMATION: Xaa is pGlu, Sar or AcSar
<220> FEATURE:
<221> NAME/KEY: SITE
<222> LOCATION: (2)
<223> OTHER INFORMATION: Xaa is His
<220> FEATURE:
<221> NAME/KEY: SITE
<222> LOCATION: (3)
<223> OTHER INFORMATION: Xaa is as defined for SEQ ID NO:1
<220> FEATURE:
<221> NAME/KEY: SITE
<222> LOCATION: (4)
<223> OTHER INFORMATION: Xaa is as defined for SEQ ID NO:1
<220> FEATURE:
<221> NAME/KEY: SITE
<222> LOCATION: (5)
<223> OTHER INFORMATION: Xaa is an aromatic L-amino acid
<220> FEATURE:
<221> NAME/KEY: SITE
<222> LOCATION: (6)
<223> OTHER INFORMATION: Xaa is Gly; D-Pro; D-Ser; D-Thr; D-Cys; D-Met;
      D-Pen; D-(S-Me)Pen; D-(S-Et)Pen; D-Ser(OBut); D-Asp(OBut);
      D-Glu(OBut); D-Thr(OBut); D- Cys(OBut); an aza-amino acid;
<220> FEATURE:
<221> NAME/KEY: SITE
<222> LOCATION: (6)
<223> OTHER INFORMATION: Xaa is D-His; an aliphatic D-amino acid with a
      (C1-C8)alkyl or a (C3-C6)cycloalkyl side chain; an aromatic
```

-continued

```
      D-amino acid; D- cyclohexadienyl-Gly;
<220> FEATURE:
<221> NAME/KEY: SITE
<222> LOCATION: (6)
<223> OTHER INFORMATION: Xaa is D-perhydronaphthyl-Ala;
      D-perhydrodiphenyl-Ala; or a basic D-amino acid
<220> FEATURE:
<221> NAME/KEY: SITE
<222> LOCATION: (7)
<223> OTHER INFORMATION: Xaa is as defined for SEQ ID NO:1
<220> FEATURE:
<221> NAME/KEY: SITE
<222> LOCATION: (8)
<223> OTHER INFORMATION: Xaa is a basic L-amino acid
<220> FEATURE:
<221> NAME/KEY: SITE
<222> LOCATION: (10)
<223> OTHER INFORMATION: Xaa is Gly or azaGly

<400> SEQUENCE: 2

Xaa Xaa Xaa Xaa Xaa Xaa Xaa Xaa Pro Xaa
  1               5                  10


<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: LH-RH
      analogue
<220> FEATURE:
<221> NAME/KEY: SITE
<222> LOCATION: (1)
<223> OTHER INFORMATION: Xaa is as defined for SEQ ID NO:1
<220> FEATURE:
<221> NAME/KEY: SITE
<222> LOCATION: (2)
<223> OTHER INFORMATION: Xaa is an aromatic D-amino acid
<220> FEATURE:
<221> NAME/KEY: SITE
<222> LOCATION: (3)
<223> OTHER INFORMATION: Xaa is as defined for SEQ ID NO:1
<220> FEATURE:
<221> NAME/KEY: SITE
<222> LOCATION: (4)
<223> OTHER INFORMATION: Xaa is as defined for SEQ ID NO:1
<220> FEATURE:
<221> NAME/KEY: SITE
<222> LOCATION: (5)
<223> OTHER INFORMATION: Xaa is as defined for SEQ ID NO:1
<220> FEATURE:
<221> NAME/KEY: SITE
<222> LOCATION: (6)
<223> OTHER INFORMATION: Xaa is Gly; D-Pro; D-Ser; D-Thr; D-Cys; D-Met;
      D-Pen; D-(S-Me)Pen; D-(S-Et)Pen; D-Ser(OBut); D-Asp(OBut);
      D-Glu(O-But); D-Thr(O-But); D-Cys(O-But);
<220> FEATURE:
<221> NAME/KEY: SITE
<222> LOCATION: (6)
<223> OTHER INFORMATION: Xaa is an aliphatic D-amino acid with a
      (C1-C8)alkyl or a (C3-C6)cycloalkyl side chain; an aromatic
      D-amino acid; D-cyclohexadienyl-Gly;
<220> FEATURE:
<221> NAME/KEY: SITE
<222> LOCATION: (6)
<223> OTHER INFORMATION: Xaa is D-perhydronaphthyl-Ala;
      D-perhydrodiphenyl-Ala; or a basic L- or D-amino acid
<220> FEATURE:
<221> NAME/KEY: SITE
<222> LOCATION: (7)
<223> OTHER INFORMATION: Xaa is as defined for SEQ ID NO:1
<220> FEATURE:
<221> NAME/KEY: SITE
<222> LOCATION: (8)
<223> OTHER INFORMATION: Xaa is as defined for SEQ ID NO:1
<220> FEATURE:
<221> NAME/KEY: SITE
```

-continued

<222> LOCATION: (10)
<223> OTHER INFORMATION: Xaa is Gly or D-Ala

<400> SEQUENCE: 3

```
Xaa Xaa Xaa Xaa Xaa Xaa Xaa Xaa Pro Xaa
  1               5                  10
```

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: LH-RH analogue
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (3)
<223> OTHER INFORMATION: Xaa is as defined for SEQ ID NO:2
<220> FEATURE:
<221> NAME/KEY: SITE
<222> LOCATION: (6)
<223> OTHER INFORMATION: Xaa is Gly; an aliphatic D-amino acid with a (C1-C8)alkyl side chain; or an aromatic D-amino acid
<220> FEATURE:
<221> NAME/KEY: SITE
<222> LOCATION: (7)
<223> OTHER INFORMATION: Xaa is as defined for SEQ ID NO:2
<220> FEATURE:
<221> NAME/KEY: SITE
<222> LOCATION: (10)
<223> OTHER INFORMATION: Xaa is Gly

<400> SEQUENCE: 4

```
Xaa His Xaa Ser Tyr Xaa Xaa Arg Pro Xaa
  1               5                  10
```

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: LH-RH analogue
<220> FEATURE:
<221> NAME/KEY: SITE
<222> LOCATION: (1)
<223> OTHER INFORMATION: Xaa is Ac-D-Nal
<220> FEATURE:
<221> NAME/KEY: SITE
<222> LOCATION: (2)
<223> OTHER INFORMATION: Xaa is D-pClPhe
<220> FEATURE:
<221> NAME/KEY: SITE
<222> LOCATION: (3)
<223> OTHER INFORMATION: Xaa is D-Pal
<220> FEATURE:
<221> NAME/KEY: SITE
<222> LOCATION: (5)
<223> OTHER INFORMATION: Xaa is as defined for SEQ ID NO:3
<220> FEATURE:
<221> NAME/KEY: SITE
<222> LOCATION: (6)
<223> OTHER INFORMATION: Xaa is Gly or a basic L- or D-amino acid
<220> FEATURE:
<221> NAME/KEY: SITE
<222> LOCATION: (7)
<223> OTHER INFORMATION: Xaa is as defined for SEQ ID NO:3
<220> FEATURE:
<221> NAME/KEY: SITE
<222> LOCATION: (8)
<223> OTHER INFORMATION: Xaa is as defined for SEQ ID NO:3

-continued

```
<220> FEATURE:
<221> NAME/KEY: SITE
<222> LOCATION: (10)
<223> OTHER INFORMATION: Xaa is D-Ala

<400> SEQUENCE: 5

Xaa Xaa Xaa Ser Xaa Xaa Xaa Xaa Pro Xaa
  1               5                  10


<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: LH-RH
      analogue
<220> FEATURE:
<221> NAME/KEY: SITE
<222> LOCATION: (1)
<223> OTHER INFORMATION: Xaa is as defined for SEQ ID NO:1
<220> FEATURE:
<221> NAME/KEY: SITE
<222> LOCATION: (2)
<223> OTHER INFORMATION: Xaa is as defined for SEQ ID NO:1
<220> FEATURE:
<221> NAME/KEY: SITE
<222> LOCATION: (3)
<223> OTHER INFORMATION: Xaa is as defined for SEQ ID NO:1
<220> FEATURE:
<221> NAME/KEY: SITE
<222> LOCATION: (4)
<223> OTHER INFORMATION: Xaa is as defined for SEQ ID NO:1
<220> FEATURE:
<221> NAME/KEY: SITE
<222> LOCATION: (5)
<223> OTHER INFORMATION: Xaa is as defined for SEQ ID NO:1
<220> FEATURE:
<221> NAME/KEY: SITE
<222> LOCATION: (6)
<223> OTHER INFORMATION: Xaa is as defined for SEQ ID NO:1
<220> FEATURE:
<221> NAME/KEY: SITE
<222> LOCATION: (7)
<223> OTHER INFORMATION: Xaa is Npg which may be N-alpha-substituted by
      a (C1-C4)alkyl group
<220> FEATURE:
<221> NAME/KEY: SITE
<222> LOCATION: (8)
<223> OTHER INFORMATION: Xaa is as defined for SEQ ID NO:1
<220> FEATURE:
<221> NAME/KEY: SITE
<222> LOCATION: (10)
<223> OTHER INFORMATION: Xaa is as defined for SEQ ID NO:1

<400> SEQUENCE: 6

Xaa Xaa Xaa Xaa Xaa Xaa Xaa Xaa Pro Xaa
  1               5                  10


<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: LH-RH
      analogue
<220> FEATURE:
<221> NAME/KEY: SITE
<222> LOCATION: (1)
<223> OTHER INFORMATION: Xaa is as defined for SEQ ID NO:2
<220> FEATURE:
<221> NAME/KEY: SITE
<222> LOCATION: (2)
<223> OTHER INFORMATION: Xaa is as defined for SEQ ID NO:2
<220> FEATURE:
<221> NAME/KEY: SITE
```

-continued

```
<222> LOCATION: (3)
<223> OTHER INFORMATION: Xaa is as defined for SEQ ID NO:2
<220> FEATURE:
<221> NAME/KEY: SITE
<222> LOCATION: (4)
<223> OTHER INFORMATION: Xaa is as defined for SEQ ID NO:2
<220> FEATURE:
<221> NAME/KEY: SITE
<222> LOCATION: (5)
<223> OTHER INFORMATION: Xaa is as defined for SEQ ID NO:2
<220> FEATURE:
<221> NAME/KEY: SITE
<222> LOCATION: (6)
<223> OTHER INFORMATION: Xaa is as defined for SEQ ID NO:2
<220> FEATURE:
<221> NAME/KEY: SITE
<222> LOCATION: (7)
<223> OTHER INFORMATION: Xaa is Npg which may be N-alpha-substituted by
      a (C1-C4)alkyl group
<220> FEATURE:
<221> NAME/KEY: SITE
<222> LOCATION: (8)
<223> OTHER INFORMATION: Xaa is as defined for SEQ ID NO:2
<220> FEATURE:
<221> NAME/KEY: SITE
<222> LOCATION: (10)
<223> OTHER INFORMATION: Xaa is as defined for SEQ ID NO:2

<400> SEQUENCE: 7

Xaa Xaa Xaa Xaa Xaa Xaa Xaa Xaa Pro Xaa
  1               5                  10


<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: LH-RH
      analogue
<220> FEATURE:
<221> NAME/KEY: SITE
<222> LOCATION: (1)
<223> OTHER INFORMATION: Xaa is as defined for SEQ ID NO:3
<220> FEATURE:
<221> NAME/KEY: SITE
<222> LOCATION: (2)
<223> OTHER INFORMATION: Xaa is as defined for SEQ ID NO:3
<220> FEATURE:
<221> NAME/KEY: SITE
<222> LOCATION: (3)
<223> OTHER INFORMATION: Xaa is as defined for SEQ ID NO:3
<220> FEATURE:
<221> NAME/KEY: SITE
<222> LOCATION: (4)
<223> OTHER INFORMATION: Xaa is as defined for SEQ ID NO:3
<220> FEATURE:
<221> NAME/KEY: SITE
<222> LOCATION: (5)
<223> OTHER INFORMATION: Xaa is as defined for SEQ ID NO:3
<220> FEATURE:
<221> NAME/KEY: SITE
<222> LOCATION: (6)
<223> OTHER INFORMATION: Xaa is as defined for SEQ ID NO:3
<220> FEATURE:
<221> NAME/KEY: SITE
<222> LOCATION: (7)
<223> OTHER INFORMATION: Xaa is Npg which may be N-alpha-substituted by
      a (C1-C4)alkyl group
<220> FEATURE:
<221> NAME/KEY: SITE
<222> LOCATION: (8)
<223> OTHER INFORMATION: Xaa is as defined for SEQ ID NO:3
<220> FEATURE:
<221> NAME/KEY: SITE
<222> LOCATION: (10)
<223> OTHER INFORMATION: Xaa is as defined for SEQ ID NO:3
```

-continued

<400> SEQUENCE: 8

```
Xaa Xaa Xaa Xaa Xaa Xaa Xaa Xaa Pro Xaa
  1               5                   10
```

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: LH-RH analogue
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (7)
<223> OTHER INFORMATION: Xaa is Npg

<400> SEQUENCE: 9

```
Xaa His Trp Ser Tyr Gly Xaa Arg Pro Gly
  1               5                   10
```

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: LH-RH analogue
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (7)
<223> OTHER INFORMATION: Xaa is Npg

<400> SEQUENCE: 10

```
Xaa His Trp Ser Tyr Gly Xaa Arg Pro
  1               5
```

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: LH-RH analogue
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (6)
<223> OTHER INFORMATION: Xaa is D-Ala
<220> FEATURE:
<221> NAME/KEY: SITE
<222> LOCATION: (7)
<223> OTHER INFORMATION: Xaa is Npg

<400> SEQUENCE: 11

```
Xaa His Trp Ser Tyr Xaa Xaa Arg Pro Gly
  1               5                   10
```

<210> SEQ ID NO 12
<211> LENGTH: 9
<212> TYPE: PRT

-continued

```
<213> ORGANISM: Artificial Sequence
<220> FEATURE:
<223> OTHER INFORMATION: Description of Artificial Sequence: LH-RH
      analogue
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (6)
<223> OTHER INFORMATION: Xaa is D-Ala
<220> FEATURE:
<221> NAME/KEY: SITE
<222> LOCATION: (7)
<223> OTHER INFORMATION: Xaa is Npg

<400> SEQUENCE: 12

Xaa His Trp Ser Tyr Xaa Xaa Arg Pro
  1               5


<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: LH-RH
      analogue
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (6)
<223> OTHER INFORMATION: Xaa is D-Leu
<220> FEATURE:
<221> NAME/KEY: SITE
<222> LOCATION: (7)
<223> OTHER INFORMATION: Xaa is Npg

<400> SEQUENCE: 13

Xaa His Trp Ser Tyr Xaa Xaa Arg Pro Gly
  1               5                  10


<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: LH-RH
      analogue
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (6)
<223> OTHER INFORMATION: Xaa is D-Leu
<220> FEATURE:
<221> NAME/KEY: SITE
<222> LOCATION: (7)
<223> OTHER INFORMATION: Xaa is Npg

<400> SEQUENCE: 14

Xaa His Trp Ser Tyr Xaa Xaa Arg Pro
  1               5


<210> SEQ ID NO 15
<211> LENGTH: 10
<212> TYPE: PRT
<213> ORGANISM: Artificial Sequence
```

-continued

<220> FEATURE:
<223> OTHER INFORMATION: Description of Artificial Sequence: LH-RH
analogue
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (6)
<223> OTHER INFORMATION: Xaa is D-Npg
<220> FEATURE:
<221> NAME/KEY: SITE
<222> LOCATION: (7)
<223> OTHER INFORMATION: Xaa is Npg

<400> SEQUENCE: 15

Xaa His Trp Ser Tyr Xaa Xaa Arg Pro Gly
1 5 10

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: LH-RH
analogue
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (6)
<223> OTHER INFORMATION: Xaa is D-Npg
<220> FEATURE:
<221> NAME/KEY: SITE
<222> LOCATION: (7)
<223> OTHER INFORMATION: Xaa is Npg

<400> SEQUENCE: 16

Xaa His Trp Ser Tyr Xaa Xaa Arg Pro
1 5

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: LH-RH
analogue
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (6)
<223> OTHER INFORMATION: Xaa is D-Phe
<220> FEATURE:
<221> NAME/KEY: SITE
<222> LOCATION: (7)
<223> OTHER INFORMATION: Xaa is Npg

<400> SEQUENCE: 17

Xaa His Trp Ser Tyr Xaa Xaa Arg Pro Gly
1 5 10

<210> SEQ ID NO 18
<211> LENGTH: 9
<212> TYPE: PRT
<213> ORGANISM: Artificial Sequence
<220> FEATURE:

-continued

<223> OTHER INFORMATION: Description of Artificial Sequence: LH-RH
analogue
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (6)
<223> OTHER INFORMATION: Xaa is D-Phe
<220> FEATURE:
<221> NAME/KEY: SITE
<222> LOCATION: (7)
<223> OTHER INFORMATION: Xaa is Npg

<400> SEQUENCE: 18

Xaa His Trp Ser Tyr Xaa Xaa Arg Pro
1 5

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: LH-RH
analogue
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (6)
<223> OTHER INFORMATION: Xaa is D-Trp
<220> FEATURE:
<221> NAME/KEY: SITE
<222> LOCATION: (7)
<223> OTHER INFORMATION: Xaa is Npg

<400> SEQUENCE: 19

Xaa His Trp Ser Tyr Xaa Xaa Arg Pro Gly
1 5 10

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: LH-RH
analogue
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (6)
<223> OTHER INFORMATION: Xaa is D-Trp
<220> FEATURE:
<221> NAME/KEY: SITE
<222> LOCATION: (7)
<223> OTHER INFORMATION: Xaa is Npg

<400> SEQUENCE: 20

Xaa His Trp Ser Tyr Xaa Xaa Arg Pro
1 5

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: LH-RH -continued

```
      analogue
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (6)
<223> OTHER INFORMATION: Xaa is D-Nal
<220> FEATURE:
<221> NAME/KEY: SITE
<222> LOCATION: (7)
<223> OTHER INFORMATION: Xaa is Npg

<400> SEQUENCE: 21

Xaa His Trp Ser Tyr Xaa Xaa Arg Pro Gly
  1               5                   10


<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: LH-RH
      analogue
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (6)
<223> OTHER INFORMATION: Xaa is D-Nal
<220> FEATURE:
<221> NAME/KEY: SITE
<222> LOCATION: (7)
<223> OTHER INFORMATION: Xaa is Npg

<400> SEQUENCE: 22

Xaa His Trp Ser Tyr Xaa Xaa Arg Pro
  1               5


<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: LH-RH
      analogue
<220> FEATURE:
<221> NAME/KEY: SITE
<222> LOCATION: (1)
<223> OTHER INFORMATION: Xaa is Ac-D-Nal
<220> FEATURE:
<221> NAME/KEY: SITE
<222> LOCATION: (2)
<223> OTHER INFORMATION: Xaa is D-pClPhe
<220> FEATURE:
<221> NAME/KEY: SITE
<222> LOCATION: (3)
<223> OTHER INFORMATION: Xaa is D-Pal
<220> FEATURE:
<221> NAME/KEY: SITE
<222> LOCATION: (5)
<223> OTHER INFORMATION: Xaa is NicLys
<220> FEATURE:
<221> NAME/KEY: SITE
<222> LOCATION: (6)
<223> OTHER INFORMATION: Xaa is D-NicLys
<220> FEATURE:
<221> NAME/KEY: SITE
<222> LOCATION: (7)
<223> OTHER INFORMATION: Xaa is Npg
<220> FEATURE:
<221> NAME/KEY: SITE
```

-continued

```
<222> LOCATION: (8)
<223> OTHER INFORMATION: Xaa is IprLys
<220> FEATURE:
<221> NAME/KEY: SITE
<222> LOCATION: (10)
<223> OTHER INFORMATION: Xaa is D-Ala

<400> SEQUENCE: 23

Xaa Xaa Xaa Ser Xaa Xaa Xaa Xaa Pro Xaa
  1               5                  10


<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: LH-RH
      analogue
<220> FEATURE:
<221> NAME/KEY: SITE
<222> LOCATION: (1)
<223> OTHER INFORMATION: Xaa is Ac-D-Nal
<220> FEATURE:
<221> NAME/KEY: SITE
<222> LOCATION: (2)
<223> OTHER INFORMATION: Xaa is D-pClPhe
<220> FEATURE:
<221> NAME/KEY: SITE
<222> LOCATION: (3)
<223> OTHER INFORMATION: Xaa is D-Pal
<220> FEATURE:
<221> NAME/KEY: SITE
<222> LOCATION: (6)
<223> OTHER INFORMATION: Xaa is D-Cit
<220> FEATURE:
<221> NAME/KEY: SITE
<222> LOCATION: (7)
<223> OTHER INFORMATION: Xaa is Npg
<220> FEATURE:
<221> NAME/KEY: SITE
<222> LOCATION: (10)
<223> OTHER INFORMATION: Xaa is D-Ala

<400> SEQUENCE: 24

Xaa Xaa Xaa Ser Tyr Xaa Xaa Arg Pro Xaa
  1               5                  10


<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: LH-RH
      analogue
<220> FEATURE:
<221> NAME/KEY: SITE
<222> LOCATION: (1)
<223> OTHER INFORMATION: Xaa is Ac-D-Nal
<220> FEATURE:
<221> NAME/KEY: SITE
<222> LOCATION: (2)
<223> OTHER INFORMATION: Xaa is D-pClPhe
<220> FEATURE:
<221> NAME/KEY: SITE
<222> LOCATION: (3)
<223> OTHER INFORMATION: Xaa is D-Pal
<220> FEATURE:
<221> NAME/KEY: SITE
<222> LOCATION: (6)
<223> OTHER INFORMATION: Xaa is D-Cit
<220> FEATURE:
<221> NAME/KEY: SITE
<222> LOCATION: (7)
<223> OTHER INFORMATION: Xaa is Npg
<220> FEATURE:
```

-continued

<221> NAME/KEY: SITE
<222> LOCATION: (8)
<223> OTHER INFORMATION: Xaa is IprLys
<220> FEATURE:
<221> NAME/KEY: SITE
<222> LOCATION: (10)
<223> OTHER INFORMATION: Xaa is D-Ala

<400> SEQUENCE: 25

Xaa Xaa Xaa Ser Tyr Xaa Xaa Xaa Pro Xaa
1 5 10

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: LH-RH analogue
<220> FEATURE:
<221> NAME/KEY: SITE
<222> LOCATION: (1)
<223> OTHER INFORMATION: Xaa is Ac-D-Nal
<220> FEATURE:
<221> NAME/KEY: SITE
<222> LOCATION: (2)
<223> OTHER INFORMATION: Xaa is D-pClPhe
<220> FEATURE:
<221> NAME/KEY: SITE
<222> LOCATION: (3)
<223> OTHER INFORMATION: Xaa is D-Pal
<220> FEATURE:
<221> NAME/KEY: SITE
<222> LOCATION: (6)
<223> OTHER INFORMATION: Xaa is D-HCit
<220> FEATURE:
<221> NAME/KEY: SITE
<222> LOCATION: (7)
<223> OTHER INFORMATION: Xaa is Npg
<220> FEATURE:
<221> NAME/KEY: SITE
<222> LOCATION: (8)
<223> OTHER INFORMATION: Xaa is IprLys
<220> FEATURE:
<221> NAME/KEY: SITE
<222> LOCATION: (10)
<223> OTHER INFORMATION: Xaa is D-Ala

<400> SEQUENCE: 26

Xaa Xaa Xaa Ser Tyr Xaa Xaa Xaa Pro Xaa
1 5 10

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: LH-RH analogue
<220> FEATURE:
<221> NAME/KEY: SITE
<222> LOCATION: (1)
<223> OTHER INFORMATION: Xaa is Ac-D-Nal
<220> FEATURE:
<221> NAME/KEY: SITE
<222> LOCATION: (2)
<223> OTHER INFORMATION: Xaa is D-pClPhe
<220> FEATURE:
<221> NAME/KEY: SITE
<222> LOCATION: (3)
<223> OTHER INFORMATION: Xaa is D-Pal
<220> FEATURE:
<221> NAME/KEY: SITE
<222> LOCATION: (6)
<223> OTHER INFORMATION: Xaa is D-HCit -continued
<220> FEATURE:
<221> NAME/KEY: SITE
<222> LOCATION: (7)
<223> OTHER INFORMATION: Xaa is Npg
<220> FEATURE:
<221> NAME/KEY: SITE
<222> LOCATION: (10)
<223> OTHER INFORMATION: Xaa is D-Ala

<400> SEQUENCE: 27

Xaa Xaa Xaa Ser Tyr Xaa Xaa Arg Pro Xaa
1 5 10

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: LH-RH analogue
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (6)
<223> OTHER INFORMATION: Xaa is D-Pal
<220> FEATURE:
<221> NAME/KEY: SITE
<222> LOCATION: (7)
<223> OTHER INFORMATION: Xaa is Npg

<400> SEQUENCE: 28

Xaa His Trp Ser Tyr Xaa Xaa Arg Pro Gly
1 5 10

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: LH-RH analogue
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (6)
<223> OTHER INFORMATION: Xaa is D-4Pal
<220> FEATURE:
<221> NAME/KEY: SITE
<222> LOCATION: (7)
<223> OTHER INFORMATION: Xaa is Npg

<400> SEQUENCE: 29

Xaa His Trp Ser Tyr Xaa Xaa Arg Pro Gly
1 5 10

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: LH-RH analogue
<220> FEATURE:
<221> NAME/KEY: SITE
<222> LOCATION: (1)
<223> OTHER INFORMATION: Xaa is pGlu
<220> FEATURE:

-continued

<221> NAME/KEY: SITE
<222> LOCATION: (6)
<223> OTHER INFORMATION: Xaa is D-HPhe
<220> FEATURE:
<221> NAME/KEY: SITE
<222> LOCATION: (7)
<223> OTHER INFORMATION: Xaa is Npg

<400> SEQUENCE: 30

Xaa His Trp Ser Tyr Xaa Xaa Arg Pro Gly
1 5 10

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: LH-RH analogue
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (6)
<223> OTHER INFORMATION: Xaa is D-Leu
<220> FEATURE:
<221> NAME/KEY: SITE
<222> LOCATION: (7)
<223> OTHER INFORMATION: Xaa is MeNpg

<400> SEQUENCE: 31

Xaa His Trp Ser Tyr Xaa Xaa Arg Pro
1 5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: LH-RH analogue
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (3)
<223> OTHER INFORMATION: Xaa is 1Nal
<220> FEATURE:
<221> NAME/KEY: SITE
<222> LOCATION: (6)
<223> OTHER INFORMATION: Xaa is D-Leu
<220> FEATURE:
<221> NAME/KEY: SITE
<222> LOCATION: (7)
<223> OTHER INFORMATION: Xaa is Npg

<400> SEQUENCE: 32

Xaa His Xaa Ser Tyr Xaa Xaa Arg Pro
1 5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: LH-RH analogue
<220> FEATURE:
<221> NAME/KEY: SITE -continued
<222> LOCATION: (1)
<223> OTHER INFORMATION: Xaa is pGlu
<220> FEATURE:
<221> NAME/KEY: SITE
<222> LOCATION: (3)
<223> OTHER INFORMATION: Xaa is 2Nal
<220> FEATURE:
<221> NAME/KEY: SITE
<222> LOCATION: (6)
<223> OTHER INFORMATION: Xaa is D-Leu
<220> FEATURE:
<221> NAME/KEY: SITE
<222> LOCATION: (7)
<223> OTHER INFORMATION: Xaa is Npg

<400> SEQUENCE: 33

Xaa His Xaa Ser Tyr Xaa Xaa Arg Pro
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: LH-RH analogue
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (3)
<223> OTHER INFORMATION: Xaa is Bal
<220> FEATURE:
<221> NAME/KEY: SITE
<222> LOCATION: (6)
<223> OTHER INFORMATION: Xaa is D-Leu
<220> FEATURE:
<221> NAME/KEY: SITE
<222> LOCATION: (7)
<223> OTHER INFORMATION: Xaa is Npg

<400> SEQUENCE: 34

Xaa His Xaa Ser Tyr Xaa Xaa Arg Pro
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: LH-RH analogue
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (6)
<223> OTHER INFORMATION: Xaa is D-Phe
<220> FEATURE:
<221> NAME/KEY: SITE
<222> LOCATION: (7)
<223> OTHER INFORMATION: Xaa is adamantyl-Ala

<400> SEQUENCE: 35

Xaa His Trp Ser Tyr Xaa Xaa Arg Pro
1               5

<210> SEQ ID NO 36
<211> LENGTH: 9

-continued

```
<212> TYPE: PRT
<213> ORGANISM: Artificial Sequence
<220> FEATURE:
<223> OTHER INFORMATION: Description of Artificial Sequence: LH-RH
      analogue
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (6)
<223> OTHER INFORMATION: Xaa is D-Ala
<220> FEATURE:
<221> NAME/KEY: SITE
<222> LOCATION: (7)
<223> OTHER INFORMATION: Xaa is adamantyl-Ala

<400> SEQUENCE: 36

Xaa His Trp Ser Tyr Xaa Xaa Arg Pro
  1               5


<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: LH-RH
      analogue
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (6)
<223> OTHER INFORMATION: Xaa is D-Leu
<220> FEATURE:
<221> NAME/KEY: SITE
<222> LOCATION: (7)
<223> OTHER INFORMATION: Xaa is adamantyl-Ala

<400> SEQUENCE: 37

Xaa His Trp Ser Tyr Xaa Xaa Arg Pro
  1               5


<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: LH-RH
      analogue
<220> FEATURE:
<221> NAME/KEY: SITE
<222> LOCATION: (1)
<223> OTHER INFORMATION: Xaa is pGlu
<220> FEATURE:
<221> NAME/KEY: SITE
<222> LOCATION: (6)
<223> OTHER INFORMATION: Xaa is D-Trp
<220> FEATURE:
<221> NAME/KEY: SITE
<222> LOCATION: (7)
<223> OTHER INFORMATION: Xaa is adamantyl-Ala

<400> SEQUENCE: 38

Xaa His Trp Ser Tyr Xaa Xaa Arg Pro Gly
  1               5                  10


<210> SEQ ID NO 39
<211> LENGTH: 10
<212> TYPE: PRT
```

-continued

```
<213> ORGANISM: Natural sequence of LH-RH
<220> FEATURE:
<221> NAME/KEY: SITE
<222> LOCATION: (1)
<223> OTHER INFORMATION: Xaa is pGlu

<400> SEQUENCE: 39

Xaa His Trp Ser Tyr Gly Leu Arg Pro Gly
  1               5                  10
```

LH-RH PEPTIDE ANALOGUES, THEIR USES AND PHARMACEUTICAL COMPOSITIONS CONTAINING THEM

This is a continuation of PCT/EP98/02802 filed May 6, 1998.

BACKGROUND OF THE INVENTION

This invention relates to LH-RH peptide analogues, to their use and to pharmaceutical compositions in which they are present.

LH-RH, or luteinizing hormone-releasing hormone, is a neurohumoral hormone produced in the hypothalamus which stimulates the secretion of the gonadotrophins, LH (luteinizing hormone) and FSH (follicle-stimulating hormone), which in turn regulate the endocrine and exocrine functions of the ovary in the female, and of the testis in the male. It has the following structural formula (SEQ ID NO: 39):

```
 1   2   3   4   5   6   7   8   9   10
pGlu-His-Trp-Ser-Tyr-Gly-Leu-Arg-Pro-Gly-NH2
```

Historically (Karten and Rivier, Endocr. Rev., 1986, 7(1), 44–66), synthetic improvement of LH-RH activity has been achieved first, by replacement of the C-terminal glycinamide by an ethylamide directly bound to $Pro^9$, and then, by introduction of D-Ala in position 6. Both independent breakthroughs yielded analogs each about 5 times more active than LH-RH. All therapeutically useful agonists result from further major improvement in position 6 with the introduction of hydrophobic aliphatic or aromatic D-amino acids instead of D-Ala, with or without the combined $Pro^9$-N-ethylamide modification. On this C-terminal end, only slight improvements have been obtained with fluorinated amides or with azaglycinamide. Replacement of Trp in position 3 by 1Nal has been reported (Karten and Rivier, 1986, cf above) to give an agonist twice as potent as LH-RH, without further synthetic or therapeutic developments.

The only other individual amino acid modification noticed to increase the biological activity of some agonists was found in position 7. Thus, N-methylation of $Leu^7$ in LH-RH itself did not increase its potency, but enhanced the activity of some already potent synthetic agonists with certain D-amino acids in position 6 such as D-Trp (Karten and Rivier, 1986, cf above); furthermore, charged and bulkier L-amino acids than leucine (Ser($OBu^t$), Asp(O-$Bu^t$), Glu(O-$Bu^t$), BocLys) somewhat improved the activity of [des-$Gly^{10}$; $Pro^9$-N-ethylamide]-LH-RH but reduced the potency of 6-modified agonists (Karten and Rivier, 1986, cf above).

As far as antagonists are concerned, numerous modifications in all positions but $Pro^9$, and a wide variety of combinations among them, have been tried with unequal success to achieve inhibition of endogenous LH-RH activity (Dutta, Drugs of the Future, 1988, 13(8), 761–787; Karten and Rivier, Endoc. Rev., 1986, 7(1), 44–66). For example, antide, a standard potent LH-RH antagonist, results from amino acid changes in positions 1, 2, 3, 5, 6, 8 and 10. N-methylation of $Leu^7$ brought about a decrease in potency, and the only changes in this position reported to increase it (2-fold maximum) were the replacement of $Leu^7$ by $Trp^7$ or $Phe^7$.

BRIEF SUMMARY OF THE INVENTION

It has now been found that the replacement of $Leu^7$ by highly hydrophobic amino acids, increases the activity of LH-RH itself or of known highly active analogues (agonists or antagonists) of LH-RH.

Especially, it has been found that the replacement of $Leu^7$ by adamantylalanine (Ada) or neopentylglycine (Npg) increases the activity of LH-RH itself and makes it possible to obtain analogs with a high affinity for the LH-RH receptors. More specifically, the [$Npg^7$]-LH-RH analogues of this invention are potent LH-RH agonists/antagonists in vivo.

DETAILED DESCRIPTION OF THE INVENTION

Thus, according to one aspect of the present invention, LH-RH peptide analogues with high affinity for the LH-RH receptors are provided, in which a non-aromatic hydrophobic amino acid having from 7 to 20 carbon atoms, such as for example $Ada^7$ or, preferably, $Npg^7$ is substituted for $Leu^7$. Preferably these peptide analogues are of the formula (SEQ ID NO: 1):

A1-A2-A3-A4-A5-A6-HAA-A7-Pro-Z (I)

in which:

- A1 is pGlu; D-pGlu; Sar; N-AcSar; Pro or a derivative thereof such as N-AcPro, ForPro, OH-Pro, Ac-OH-Pro, dehydro-Pro or Ac-dehydro-Pro; Ser; D-Ser; Ac-D-Ser; Thr; D-Thr; Ac-D-Thr; or an aromatic D-amino acid which may be acylated, such as D-Phe, D-HPhe, D-Tyr, D-Trp, D-Nal, D-1Nal, D-diphenyl-Ala, D-Bal, D-Pal, D-4Pal or D-Qal, where D-Phe and D-Trp may be substituted by one or more halogens, $(C_1–C_4)$alkyl, $(C_1–C_4)$alkoxy, nitro or trifluoromethyl groups;
- A2 is a direct bond; His; or an aromatic D-amino acid such as D-Phe, D-HPhe, D-Tyr, D-Trp, D-Nal, D-1Nal, D-diphenyl-Ala, D-Bal, D-Pal, D-4Pal or D-Qal, where D-Phe and D-Trp may be substituted by one or more halogens, $(C_1–C_4)$alkyl, $(C_1–C_4)$alkoxy, nitro or trifluoromethyl groups;
- A3 is an aromatic L- or D-amino acid such as Phe, HPhe, Tyr, Trp, Nal, 1Nal, diphenyl-Ala, Bal, Pal, 4Pal or Qal, where Phe and Trp may be substituted by one or more halogens, $(C_1–C_4)$alkyl, $(C_1–C_4)$alkoxy, nitro or trifluoromethyl groups;
- A4 is Ala, Ser, D-Ser, N-MeSer, Ser($OBu^t$), Ser(OBzl) or Thr;
- A5 is an aromatic L-amino acid such as Phe, HPhe, Tyr, Trp, Nal, 1Nal, diphenyl-Ala, Bal, Pal, 4Pal or Qal, where Phe and Trp may be substituted by one or more halogens, $(C_1–C_4)$alkyl, $(C_1–C_4)$alkoxy, nitro or trifluoromethyl groups; or a basic L- or D-amino acid such as Arg, HArg, Orn, Lys, HLys, Cit, HCit, APhe or ACha, where Arg and HArg may be N-substituted by a $(C_1–C_6)$alkyl or a $(C_3–C_6)$cycloalkyl group on one or both nitrogen atoms, and where Orn, Lys, HLys, APhe and ACha may be N-substituted by one or two $(C_1–C_6)$ alkyl or $(C_3–C_6)$cycloalkyl groups, or by a nicotinoyl, isonicotinoyl, 6-methyl-nicotinoyl, glycyl-nicotinoyl, nicotinyl-azaglycyl, furyl, glycyl-furyl, furyl-azaglycyl, pyrazinyl, pyrazinyl-carbonyl, picolinoyl, 6-methyl-picolinoyl, shikimyl, shikimyl-glycyl, Fmoc or Boc group;

A6 is Gly; D-Pro; D-Ser; D-Thr; D-Cys; D-Met; D-Pen; D-(S-Me)Pen; D-(S-Et)Pen; D-Ser($OBu^t$); D-Asp($OBu^t$); D-Glu($OBu^t$); D-Thr($OBu^t$); D-Cys($OBu^t$); D-Ser($OR_1$) where $R_1$ is a sugar moiety; an aza-amino acid such as azaGly or azaAla; D-His which may be substituted on the imidazole ring by a $(C_1–C_6)$alkyl or by a $(C_2–C_7)$acyl group;

an aliphatic D-amino acid with a $(C_1-C_8)$alkyl or a $(C_3-C_6)$ cycloalkyl side chain such as D-Ala, D-Abu, D-Aib, D-3Aib, D-Val, D-Nva, D-Leu, D-Ile, D-Tle, D-Nle, D-Hol, D-Npg, D-CPa, D-Cpa, D-Cba or D-Cha; an aromatic D-amino acid such as D-Phe, D-HPhe, D-Tyr, D-Trp, D-Nal, D-1Nal, D-diphenyl-Ala, D-anthryl-Ala, D-phenanthryl-Ala, D-benzhydryl-Ala, D-fluorenyl-Ala, D-Bal, D-Pal, D-4Pal or D-Qal, where D-Phe and D-Trp may be substituted by one or more halogens, $(C_1-C_4)$alkyl, $(C_1-C_4)$ alkoxy, nitro or trifluoromethyl groups; D-cyclohexadienyl-Gly; D-perhydronaphthyl-Ala; D-perhydrodiphenyl-Ala; or a basic L- or D-amino acid such as Arg, HArg, Orn, Lys, HLys, Cit, HCit, APhe or ACha, where Arg and HArg may be N-substituted by a $(C_1-C_6)$aLkyl or a $(C_3-C_6)$cycloalkyl group on one or both nitrogen atoms, and where Orn, Lys, HLys, APhe and ACha may be N-substituted by one or two $(C_1-C_6)$alkyl or $(C_3-C_6)$cycloalkyl groups, or by a nicotinoyl, isonicotinoyl, 6-methyl-nicotinoyl, glycyl-nicotinoyl, nicotinyl-azaglycyl, furyl, glycyl-furyl, furyl-azaglycyl, pyrazinyl, pyrazinyl-carbonyl, picolinoyl, 6-methyl-picolinoyl, shikimyl, shikimyl-glycyl, Fmoc or Boc group;

HAA is a non-aromatic hydrophobic amino acid of from 7 to 20 carbon atoms;

A7 is a basic L- or D-amino acid such as Arg, HArg, Orn, Lys, HLys, Cit, HCit, APhe or ACha, where Arg or HArg may be N-substituted by a $(C_1-C_6)$alkyl or a $(C_3-C_6)$cycloalkyl group on one or both nitrogen atoms, and where Orn, Lys, HLys, APhe or ACha may be N-substituted by one or two $(C_1-C_6)$alkyl or $(C_3-C_6)$cycloalkyl groups, or by a nicotinoyl, isonicotinoyl, 6-methyl-nicotinoyl, glycyl-nicotinoyl, nicotinyl-azaglycyl, furyl, glycyl-furyl, furyl-azaglycyl, pyrazinyl, pyrazinyl-carbonyl, picolinoyl, 6-methyl-picolinoyl, shikimyl, shikimyl-glycyl, Fmoc or Boc group;

Z is $GlyNH_2$; D-$AlaNH_2$; aza$GlyNH_2$; or a group $—NHR_2$ where $R_2$ is a $(C_1-C_4)$alkyl which may be substituted by an hydroxy or one or several fluorine atoms, a $(C_3-C_6)$cycloalkyl, or a heterocyclic radical selected from morpholinyl, pyrrolidinyl and piperidyl;

as well as their pharmaceutically acceptable salts.

In these peptide analogues, HAA is preferably Ada or Npg which may be N-alpha-substituted by a $(C_1-C_4)$-alkyl group optionally substituted by one or several fluorine atoms, Npg being especially preferred.

A preferred group of peptide analogues (I) comprises the peptides of the formula (SEQ ID NO: 6):

A1-A2-A3-A4-A5-A6-Npg-A7-Pro-Z (I')

in which:

A1 is pGlu; D-pGlu; Sar; N-AcSar; Pro or a derivative thereof such as N-AcPro, ForPro, OH-Pro, Ac-OH-Pro, dehydro-Pro or Ac-dehydro-Pro; Ser; D-Ser; Ac-D-Ser; Thr; D-Thr; Ac-D-Thr; or an aromatic D-amino acid which may be acylated, such as D-Phe, D-Tyr, D-Trp, D-Nal, D-1Nal, D-diphenyl-Ala, D-Bal, D-Pal or D-Qal, where D-Phe and D-Trp may be substituted by one or more halogens, $(C_1-C_4)$alkyl, $(C_1-C_4)$alkoxy, nitro or trifluoromethyl groups;

A2 is a direct bond; His; or an aromatic D-amino acid such as D-Phe, D-Tyr, D-Trp, D-Nal, D-1Nal, D-diphenyl-Ala, D-Bal, D-Pal or D-Qal, where D-Phe and D-Trp may be substituted by one or more halogens, $(C_1-C_4)$alkyl, $(C_1-C_4)$alkoxy, nitro or trifluoromethyl groups;

A3 is an aromatic L- or D-amino acid such as Phe, Tyr, Trp, Nal, 1Nal, diphenyl-Ala, Bal, Pal or Qal, where Phe and Trp may be substituted by one or more halogens, $(C_1-C_4)$alkyl, $(C_1-C_4)$alkoxy, nitro or trifluoromethyl groups;

A4 is Ala, Ser, D-Ser, N-MeSer, Ser($OBu^t$), Ser(OBzl) or Thr;

A5 is an aromatic L-amino acid such as Phe, Tyr, Trp, Nal, 1Nal, diphenyl-Ala, Bal, Pal or Qal, where Phe and Trp may be substituted by one or more halogens, $(C_1-C_4)$ alkyl, $(C_1-C_4)$alkoxy, nitro or trifluoromethyl groups; or a basic L- or D-amino acid such as Arg, HArg, Orn, Lys, HLys, Cit, HCit, APhe or ACha, where Arg and HArg may be N-substituted by a $(C_1-C_6)$alkyl or a $(C_3-C_6)$cycloalkyl group on one or both nitrogen atoms, and where Orn, Lys, HLys, APhe and ACha may be N-substituted by one or two $(C_1-C_6)$alkyl or $(C_3-C_6)$cycloalkyl groups, or by a nicotinoyl, isonicotinoyl, 6-methyl-nicotinoyl, glycyl-nicotinoyl, nicotinyl-azaglycyl, furyl, glycyl-furyl, furyl-azaglycyl, pyrazinyl, pyrazinyl-carbonyl, picolinoyl, 6-methyl-picolinoyl, shikimyl, shikimyl-glycyl, Fmoc or Boc group;

A6 is Gly; D-Pro; D-Ser; D-Thr; D-Cys; D-Met; D-Pen; D-(S-Me)Pen; D-(S-Et)Pen; D-Ser($OBu^t$); D-Asp ($OBu^t$); D-Glu($OBu^t$); D-Thr($OBu^t$); D-Cys($OBu^t$); D-Ser($OR_1$) where $R_1$ is a sugar moiety; an aza-amino acid such as azaGly or azaAla; D-His which may be substituted on the imidazole ring by a $(C_1-C_6)$alkyl or by a $(C_2-C_7)$acyl group; an aliphatic D-amino acid with a $(C_1-C_8)$alkyl or a $(C_3-C_6)$cycloalkyl side chain such as D-Ala, D-Abu, D-Aib, D-3Aib, D-Val, D-Nva, D-Leu, D-Ile, D-Tle, D-Nle, D-Hol, D-Npg, D-CPa, D-Cpa, D-Cba or D-Cha; an aromatic D-amino acid such as D-Phe, D-Tyr, D-Trp, D-Nal, D-1Nal, D-diphenyl-Ala, D-anthryl-Ala, D-phenanthryl-Ala, D-benzhydryl-Ala, D-fluorenyl-Ala, D-Bal, D-Pal or D-Qal, where D-Phe and D-Trp may be substituted by one or more halogens, $(C_1-C_4)$alkyl, $(C_1-C_4)$alkoxy, nitro or trifluoromethyl groups; D-cyclohexadienyl-Gly; D-perhydronaphthyl-Ala; D-perhydrodiphenyl-Ala; or a basic L- or D-amino acid such as Arg, HArg, Orn, Lys, HLys, Cit, HCit, APhe or ACha, where Arg and HArg may be N-substituted by a $(C_1-C_6)$alkyl or a $(C_3-C_6)$cycloalkyl group on one or both nitrogen atoms, and where Orn, Lys, HLys, APhe and ACha may be N-substituted by one or two $(C_1-C_6)$alkyl or $(C_3-C_6)$cycloalkyl groups, or by a nicotinoyl, isonicotinoyl, 6-methyl-nicotinoyl, glycyl-nicotinoyl, nicotinyl-azaglycyl, furyl, glycyl-furyl, furyl-azaglycyl, pyrazinyl, pyrazinyl-carbonyl, picolinoyl, 6-methyl-picolinoyl, shikimyl, shikimyl-glycyl, Fmoc or Boc group;

Npg may be N-alpha-substituted by a $(C_1-C_4)$alkyl group which may be substituted by one or several fluorine atoms;

A7 is a basic L- or D-amino acid such as Arg, HArg, Orn, Lys, HLys, Cit, HCit, APhe or ACha, where Arg or HArg may be N-substituted by a $(C_1-C_6)$alkyl or a $(C_3-C_6)$cycloalkyl group on one or both nitrogen atoms, and where Orn, Lys, HLys, APhe or ACha may be N-substituted by one or two $(C_1-C_6)$alkyl or $(C_3-C_6)$cycloalkyl groups, or by a nicotinoyl, isonicotinoyl, 6-methyl-nicotinoyl, glycyl-nicotinoyl, nicotinyl-azaglycyl, furyl, glycyl-furyl, furyl-azaglycyl, pyrazinyl, pyrazinyl-carbonyl, picolinoyl, 6-methyl-picolinoyl, shikimyl, shikimyl-glycyl, Fmoc or Boc group;

Z is $GlyNH_2$; D-$AlaNH_2$; aza$GlyNH_2$; or a group —$NHR_2$ where $R_2$ is a $(C_1-C_4)$alkyl which may be substituted by an hydroxy or one or several fluorine atoms, a $(C_3-C_6)$cycloalkyl, or a heterocyclic radical selected from morpholinyl, pyrrolidinyl and piperidyl;

as well as their pharmaceutically acceptable salts.

In the present description the term "$(C_1-C_4)$alkyl" denotes methyl, ethyl, n-propyl, i-propyl, n-butyl, i-butyl, s-butyl and t-butyl groups.

The term "$(C_1-C_6)$alkyl" denotes methyl, ethyl, n-propyl, i-propyl, n-butyl, i-butyl, s-butyl, t-butyl, n-pentyl, i-pentyl, s-pentyl, t-pentyl and hexyl groups.

The term "$(C_1-C_8)$alkyl" denotes methyl, ethyl, n-propyl, i-propyl, n-butyl, i-butyl, s-butyl, t-butyl, n-pentyl, i-pentyl, s-pentyl, t-pentyl, hexyl, heptyl and octyl groups;

The term "$(C_1-C_4)$alkoxy" denotes a group —OR where R is a $(C_1-C_4)$alkyl.

The term "$(C_2-C_7)$acyl" denotes a group —COR where R is a $(C_1-C_6)$alkyl.

The term "$(C_3-C_6)$cycloalkyl" denotes cyclopropyl, cyclobutyl, cyclopentyl and cyclohexyl groups.

The term "sugar moiety" denotes D- or L-pentoses or hexoses and their amino-derivatives.

The term "LH-RH analogues" denotes peptides in which at least one amino acid has been modified in the sequence of LH-RH.

The term "non-aromatic hydrophobic amino acid" denotes a linear, branched or cyclic amino acid with a side chain of from 5 to 18, more preferably 5 to 11 carbon atoms (beginning at the β-carbon included); the hydrophobic nature of a suitable amino-acid can be defined by a positive difference of at least 0.5 when compared with leucine, in either log P (P: partition coefficient in the n-octanol/water system) or the Hansch hydrophobicity constant π.

In the present description and in the claims, the following abbreviations are used:

| | |
|---|---|
| Abu: | 2-aminobutyric acid |
| Ac: | acetyl |
| ACha: | aminocyclohexylalanine |
| Aib: | 2-aminoisobutyric acid |
| 3Aib: | 3-aminoisobutyric acid |
| Ala: | alanine |
| $AlaNH_2$: | alaninamide |
| APhe: | p-aminophenylalanine |
| Arg: | arginine |
| Asp: | aspartic acid |
| azaAla: | aza-alanine |
| azaGly: | aza-glycine |
| aza$GlyNH_2$: | azaglycinamide |
| Bal: | benzothienylalanine |
| Boc: | tert-butoxycarbonyl |
| Cba: | cyclobutylalanine |
| Cha: | cyclohexylalanine |
| Cit: | citrulline |
| CPa: | cyclopropylalanine |
| Cpa: | cylopentylalanine |
| Fmoc: | fluorenylmethoxycarbonyl |
| For: | formyl |
| Glu: | glutamic acid |
| Gly: | glycine |
| $GlyNH_2$: | glycinamide |
| HArg: | homoarginine |
| HCit: | homocitrulline |
| His: | histidine |
| HLys: | homolysine |
| Hol: | homoleucine |
| Ile: | isoleucine |

-continued

| | |
|---|---|
| IprLys: | $N^{\epsilon}$-isopropyllysine |
| Leu: | leucine |
| Lys: | lysine |
| MeSer: | N-methylserine |
| Met: | methionine |
| Nal: | 3-(2-naphtyl)alanine |
| 1Nal: | 3-(1-naphtyl)alanine |
| NEt: | N-ethylamide |
| NicLys: | $N^{\epsilon}$-nicotinoyllysine |
| Nle: | norleucine |
| Npg: | neopentylglycine |
| Nva: | norvaline |
| $OBu^t$: | tert-butoxy |
| OBzl: | benzyl ester |
| Orn: | ornithine |
| Pal: | 3-(3-pyridyl)alanine |
| pClPhe: | 3-(4-chlorophenyl)alanine |
| Pen: | penicillamine |
| pGlu: | pyroglutamic acid |
| Phe: | phenylalanine |
| Pro: | proline |
| Qal: | 3-(3-quinolyl)alanine |
| Sar: | sarcosine |
| Ser: | serine |
| (S-Me)Pen: | S-methyl-penicillamine |
| (S-Et)Pen: | S-ethyl-penicillamine |
| Thr: | threonine |
| Tle: | tert-leucine |
| Trp: | tryptophan |
| Tyr: | tyrosine |
| Val: | valine |
| Ada: | adamantylalanine |
| HPhe: | homophenylalanine |
| MeNpg: | N-methylneopentylglycine |
| 4Pal: | 3-(4-pyridyl)alanine |

A preferred group of peptide analogues according to the invention, having LH-RH agonist activity, comprises the peptides of the formula (SEQ ID NO: 2):

A1-A2-A3-A4-A5-A6-HAA-A7-Pro-Z (IIa)

in which:

A1 is pGlu, Sar or N-AcSar;

A2 is His;

A3 is an aromatic L-amino acid such as Phe, HPhe, Tyr, Trp, Nal, 1Nal, diphenyl-Ala, Bal, Pal, 4Pal or Qal, where Phe and Trp may be substituted by one or more halogens, $(C_1-C_4)$alkyl, $(C_1-C_4)$alkoxy, nitro or trifluoromethyl groups;

A4 is Ala, Ser, D-Ser, N-MeSer, Ser($OBu^t$), Ser(OBzl) or Thr;

A5 is an aromatic L-amino acid such as Phe, Hphe, Tyr, Trp, Nal, 1Nal, diphenyl-Ala, Bal, Pal, 4Pal or Qal, where Phe and Trp may be substituted by one or more halogens, $(C_1-C_4)$alkyl, $(C_1-C_4)$alkoxy, nitro or trifluoromethyl groups;

A6 is Gly; D-Pro; D-Ser; D-Thr; D-Cys; D-Met; D-Pen; D-(S-Me)Pen; D-(S-Et)Pen; D-Ser($OBu^t$); D-Asp ($OBu^t$); D-Glu($OBu^t$); D-Thr($OBu^t$); D-Cys($OBu^t$); D-Ser($OR_1$) where $R_1$ is a sugar moiety; an aza-amino acid such as azaGly or azaAla; D-His which may be substituted on the imidazole ring by a $(C_1-C_6)$alkyl or by a $(C_2-C_7)$acyl group; an aliphatic D-amino acid with a $(C_1-C_8)$alkyl or a $(C_3-C_6)$cycloalkyl side chain such as D-Ala, D-Abu, D-Aib, D-3Aib, D-Val, D-Nva, D-Leu, D-Ile, D-Tle, D-Nle, D-Hol, D-Npg, D-CPa, D-Cpa, D-Cba or D-Cha; an aromatic D-amino acid such as D-Phe, D-HPhe, D-Tyr, D-Trp, D-Nal, D-1Nal, D-diphenyl-Ala, D-anthryl-Ala, D-phenanthryl-Ala, D-benzhydryl-Ala, D-fluorenyl-Ala, D-Bal, D-Pal, D-4Pal or D-Qal, where D-Phe and D-Trp may be substituted by one or more halogens, $(C_1-C_4)$alkyl, $(C_1-C_4)$alkoxy, nitro or trifluoromethyl groups; D-cyclohexadienyl-Gly; D-perhydronaphthyl-Ala; D-perhydrodiphenyl-Ala; or a basic D-amino acid such as D-Arg, D-HArg, D-Orn, D-Lys, D-HLys, D-Cit, D-HCit, D-APhe or D-ACha, where D-Arg and D-HArg may be N-substituted by a $(C_1-C_6)$alkyl or a $(C_3-C_6)$cycloalkyl group on one or both nitrogen atoms, and where D-Orn, D-Lys, D-HLys, D-APhe and D-ACha may be N-substituted by one or two $(C_1-C_6)$ alkyl or $(C_3-C_6)$cycloalkyl groups, or by a Fmoc or Boc group;

HAA is as defined for (I);

A7 is a basic L-amino acid such as Arg, HArg, Orn, Lys, HLys, Cit, HCit, APhe or ACha;

Z is $GlyNH_2$; $azaGlyNH_2$; or a group —$NHR_2$ where $R_2$ is a $(C_1-C_4)$alkyl which may be substituted by an hydroxy or one or several fluorine atoms, a $(C_3-C_6)$ cycloalkyl or a heterocyclic radical selected from morpholinyl, pyrrolidinyl and piperidyl;

as well as their pharmaceutically acceptable salts.

In these peptide analogues, HAA is preferably Ada or Npg which may be N-alpha-substituted by a $(C_1-C_4)$alkyl group optionally substituted by one or several fluorine atoms, Npg being especially preferred.

A preferred group of peptide analogues (IIa) comprises the peptides of the formula (SEQ ID NO: 7):

A1-A2-A3-A4-A5-A6-Npg-A7-Pro-Z (II'a)

in which:

A1 is pGlu, Sar or N-AcSar;

A2 is His;

A3 is an aromatic L-amino acid such as Phe, Tyr, Trp, Nal, 1Nal, diphenyl-Ala, Bal, Pal or Qal, where Phe and Trp may be substituted by one or more halogens, $(C_1-C_4)$ alkyl, $(C_1-C_4)$alkoxy, nitro or trifluoromethyl groups;

A4 is Ala, Ser, D-Ser, MeSer, Ser($OBu^t$), Ser(OBzl) or Thr;

A5 is an aromatic L-amino acid such as Phe, Tyr, Trp, Nal, 1Nal, diphenyl-Ala, Bal, Pal or Qal, where Phe and Trp may be substituted by one or more halogens, $(C_1-C_4)$alkyl, $(C_1-C_4)$alkoxy, nitro or trifluoromethyl groups;

A6 is Gly; D-Pro; D-Ser; D-Thr; D-Cys; D-Met; D-Pen; D-(S-Me)Pen; D-(S-Et)Pen; D-Ser($OBu^t$); D-Asp ($OBu^t$); D-Glu($OBu^t$); D-Thr($OBu^t$); D-Cys($OBu^t$); D-Ser($OR_1$) where $R_1$ is a sugar moiety; an aza-amino acid such as azaGly or azaala; D-His which may be substituted on the imidazole ring by a $(C_1-C_6)$alkyl or by a $(C_2-C_7)$acyl group; an aliphatic D-amino acid with a $(C_1-C_8)$alkyl or a $(C_3$-C6)cycloalkyl side chain such as D-Ala, D-Abu, D-Aib, D-3Aib, D-Val, D-Nva, D-Leu, D-Ile, D-Tle, D-Nle, D-Hol, D-Npg, D-CPa, D-Cpa, D-Cba or D-Cha; an aromatic D-amino acid such as D-Phe, D-Tyr, D-Trp, D-Nal, D-1Nal, D-diphenyl-Ala, D-anthryl-Ala, D-phenanthryl-Ala, D-benzhydryl-Ala, D-fluorenyl-Ala, D-Bal, D-Pal or D-Qal, where D-Phe and D-Trp may be substituted by one or more halogens, $(C_1-C_4)$alkyl, $(C_1-C_4)$alkoxy, nitro or trifluoromethyl groups; D-cyclohexadienyl-Gly; D-perhydronaphthyl-Ala; D-perhydrodiphenyl-Ala; or a basic D-amino acid such as D-Arg, D-HArg, D-Orn, D-Lys, D-HLys, D-Cit, D-HCit, D-APhe or D-ACha, where D-Arg and D-HArg may be N-substituted by a $(C_1-C_6)$alkyl or a $(C_3-C_6)$ cycloalkyl group on one or both nitrogen atoms, and where D-Orn, D-Lys, D-HLys, D-APhe and D-ACha may be N-substituted by one or two $(C_1-C_6)$alkyl or $(C_3-C_6)$cycloalkyl groups, or by a Fmoc or Boc group;

Npg may be N-alpha-substituted by a $(C_1-C_4)$alkyl group which may be substituted by one or several fluorine atoms;

A7 is a basic L-amino acid such as Arg, HArg, Orn, Lys, HLys, Cit, HCit, APhe or ACha;

Z is $GlyNH_2$; azaGlyNH2; or a group —$NHR_2$ where $R_2$ is a $(C_1-C_4)$alkyl which may be substituted by an hydroxy or one or several fluorine atoms, a $(C_3-C_6)$ cycloalkyl or a heterocyclic radical selected from morpholinyl, pyrrolidinyl and piperidyl;

as well as their pharmaceutically acceptable salts.

Another preferred group of peptide analogues according to the invention, having LH-RH antagonistic activity, comprises the peptides of the formula (SEQ ID NO: 3):

A1-A2-A3-A4-A5-A6-HAA-A7-Pro-Z (IIb)

in which:

A1 is pGlu; D-pGlu; Sar; N-AcSar; Pro or a derivative thereof such as AcPro, ForPro, OH-Pro, Ac-OH-Pro, dehydro-Pro or Ac-dehydro-Pro; Ser; D-Ser; Ac-D-Ser; Thr; D-Thr; Ac-D-Thr; or an aromatic D-amino acid which may be acylated such as D-Phe, D-HPhe, D-Tyr, D-Trp, D-Nal, D-1Nal, D-diphenyl-Ala, D-Bal, D-Pal, D-4Pal or D-Qal, where D-Phe and D-Trp may be substituted by one or more halogens, $(C_1-C_4)$alkyl, $(C_1-C_4)$alkoxy, nitro or trifluoromethyl groups;

A2 is a direct bond or an aromatic D-amino acid such as D-Phe, D-HPhe, D-Tyr, D-Trp, D-Nal, D-1Nal, D-diphenyl-Ala, D-Bal, D-Pal, D-4Pal or D-Qal, where D-Phe and D-Trp may be substituted by one or more halogens, $(C_1-C_4)$alkyl, $(C_1-C_4)$alkoxy, nitro or trifluoromethyl groups;

A3 is an aromatic L- or D-amino acid such as Phe, HPhe, Tyr, Trp, Nal, 1Nal, diphenyl-Ala, Bal, Pal, 4Pal or Qal, where Phe and Trp may be substituted by one or more halogens, $(C_1-C_4)$alkyl, $(C_1-C_4)$alkoxy, nitro or trifluoromethyl groups;

A4 is Ala, Ser, D-Ser, N-MeSer, Ser($OBu^t$), Ser(OBzl) or Thr;

A5 is an aromatic L-amino acid such as Phe, HPhe, Tyr, Trp, Nal, 1Nal, diphenyl-Ala, Bal, Pal, 4Pal or Qal, where Phe and Trp may be substituted by one or more halogens, $(C_1-C_4)$alkyl, $(C_1-C_4)$alkoxy, nitro or trifluoromethyl groups; or a basic L- or D-amino acid such as Arg, HArg, Orn, Lys, HLys, Cit, HCit, APhe or ACha, where Arg and HArg may be N-substituted by a $(C_1-C_6)$alkyl or $(C_3-C_6)$cycloalkyl group on one or both nitrogen atoms, and where Orn, Lys, HLys, APhe and ACha may be N-substituted by one or two $(C_1-C_6)$ alkyl or $(C_3-C_6)$cycloalkyl groups, or by a nicotinoyl, isonicotinoyl, 6-methyl-nicotinoyl, glycyl-nicotinoyl, nicotinyl-azaglycyl, furyl, glycyl-furyl, furyl-azaglycyl, pyrazinyl, pyrazinyl-carbonyl, picolinoyl, 6-methyl-picolinoyl, shikimyl, shikimyl-glycyl, Fmoc or Boc group;

A6 is Gly; D-Pro; D-Ser; D-Thr; D-Cys; D-Met; D-Pen; D-(S-Me)Pen; D-(S-Et)Pen; D-Ser($OBu^t$); D-Asp ($OBu^t$); D-Glu(O-$Bu^t$); D-Thr(O-$Bu^t$); D-Cys(O-$Bu^t$); D-Ser(O-$R_1$) where $R_1$ is a sugar moiety; an aliphatic D-amino acid with a $(C_1-C_8)$alkyl or a $(C_3-C_6)$ cycloalkyl side chain such as D-Ala, D-Abu, D-Aib, D-3Aib, D-Val, D-Nva, D-Leu, D-Ile, D-Tle, D-Nle, D-Hol, D-Npg, D-CPa, D-Cpa, D-Cba or D-Cha; an aromatic D-amino acid such as D-Phe, D-HPhe, D-Tyr, D-Trp, D-Nal, D-1Nal, D-diphenyl-Ala, D-anthryl-Ala, D-phenanthryl-Ala, D-benzhydryl-Ala, D-fluorenyl-Ala, D-Bal, D-Pal, D-4Pal or D-Qal, where D-Phe and D-Trp may be substituted by one or more halogens, ($C_1$–$C_4$)alkyl, ($C_1$–$C_4$)alkoxy, nitro or trifluoromethyl groups; D-cyclohexadienyl-Gly; D-perhydronaphthyl-Ala; D-perhydrodiphenyl-Ala; or a basic L- or D-amino acid such as Arg, HArg, Orn, Lys, HLys, Cit, HCit, APhe or ACha, where Arg and HArg may be N-substituted by a ($C_1$–$C_6$)alkyl or ($C_3$–$C_6$)cycloalkyl group on one or both nitrogen atoms, and where Orn, Lys, HLys, APhe and ACha may be N-substituted by one or two ($C_1$–$C_6$)alkyl or ($C_3$–$C_6$)cycloalkyl groups, or by a nicotinoyl, isonicotinoyl, 6-methyl-nicotinoyl, glycyl-nicotinoyl, nicotinyl-azaglycyl, furyl, glycyl-furyl, furyl-azaglycyl, pyrazinyl, pyrazinyl-carbonyl, picolinoyl, 6-methyl-picolinoyl, shikimyl, shikimyl-glycyl, Fmoc or Boc group;

HAA is as defined for (I);

A7 is a basic L- or D-amino acid such as Arg, HArg, Orn, Lys, HLys, Cit, HCit, APhe or ACha, where Arg and HArg may be N-substituted by a ($C_1$–$C_6$)alkyl or ($C_3$–$C_6$)cycloalkyl group on one or both nitrogen atoms, and where Orn, Lys, HLys, APhe and ACha may be N-substituted by one or two ($C_1$–$C_6$)alkyl or ($C_3$–$C_6$)cycloalkyl groups, or by a nicotinoyl, isonicotinoyl, 6-methyl-nicotinoyl, glycyl-nicotinoyl, nicotinyl-azaglycyl, furyl, glycyl-furyl, furyl-azaglycyl, pyrazinyl, pyrazinyl-carbonyl, picolinoyl, 6-methyl-picolinoyl, shikimyl, shikimyl-glycyl, Fmoc or Boc group;

Z is $GlyNH_2$ or $D\text{-}AlaNH_2$;

as well as their pharmaceutically acceptable salts.

In these peptide analogues, HAA is preferably Ada or Npg which may be N-alpha-substituted by a ($C_1$–$C_4$)alkyl group optionally substituted by one or several fluorine atoms, Npg being especially preferred.

A preferred group of peptide analogues (IIb) comprises the peptides of the formula (SEQ ID NO: 8):

A1-A2-A3-A4-A5-A6-Npg-A7-Pro-Z (II'b)

in which:

A1 is pGlu; D-pGlu; Sar; N-AcSar; Pro or a derivative thereof such as AcPro, ForPro, OH-Pro, Ac-OH-Pro, dehydro-Pro or Ac-dehydro-Pro; Ser; D-Ser; Ac-D-Ser; Thr; D-Thr; Ac-D-Thr; or an aromatic D-amino acid which may be acylated such as D-Phe, D-Tyr, D-Trp, D-Nal, D-1Nal, D-diphenyl-Ala, D-Bal, D-Pal or D-Qal, where D-Phe and D-Trp may be substituted by one or more halogens, ($C_1$–$C_4$)alkyl, ($C_1$–$C_4$)alkoxy, nitro or trifluoromethyl groups;

A2 is a direct bond or an aromatic D-amino acid such as D-Phe, D-Tyr, D-Trp, D-Nal, D-1Nal, D-diphenyl-Ala, D-Bal, D-Pal or D-Qal, where D-Phe and D-Trp may be substituted by one or more halogens, ($C_1$–$C_4$)alkyl, ($C_1$–$C_4$)alkoxy, nitro or trifluoromethyl groups;

A3 is an aromatic L- or D-amino acid such as Phe, Tyr, Trp, Nal, 1Nal, diphenyl-Ala, Bal, Pal or Qal, where Phe and Trp may be substituted by one or more halogens, ($C_1$–$C_4$)alkyl, ($C_1$–$C_4$)alkoxy, nitro or trifluoromethyl groups;

A4 is Ala, Ser, D-Ser, N-MeSer, Ser(OBu$^t$), Ser(OBzl) or Thr;

A4 is Ala, Ser, D-Ser, MeSer, Ser(OBu$^t$), Ser(OBzl) or Thr;

A5 is an aromatic L-amino acid such as Phe, Tyr, Trp, Nal, 1Nal, diphenyl-Ala, Bal, Pal or Qal, where Phe and Trp may be substituted by one or more halogens, ($C_1$–$C_4$) alkyl, ($C_1$–$C_4$)alkoxy, nitro or trifluoromethyl groups; or a basic L- or D-amino acid such as Arg, HArg, Orn, Lys, HLys, Cit, HCit, APhe or ACha, where Arg and HArg may be N-substituted by a ($C_1$–$C_6$)alkyl or ($C_3$–$C_6$)cycloalkyl group on one or both nitrogen atoms, and where Orn, Lys, HLys, APhe and ACha may be N-substituted by one or two ($C_1$–$C_6$)alkyl or ($C_3$–$C_6$)cycloalkyl groups, or by a nicotinoyl, isonicotinoyl, 6-methyl-nicotinoyl, glycyl-nicotinoyl, nicotinyl-azaglycyl, furyl, glycyl-furyl, furyl-azaglycyl, pyrazinyl, pyrazinyl-carbonyl, picolinoyl, 6-methyl-picolinoyl, shikimyl, shikimyl-glycyl, Fmoc or Boc group;

A6 is Gly; D-Pro; D-Ser; D-Thr; D-Cys; D-Met; D-Pen; D-(S-Me)Pen; D-(S-Et)Pen; D-Ser(OBu$^t$); D-Asp (OBu$^t$); D-Glu(O-Bu$^t$); D-Thr(O-Bu$^t$); D-Cys(O-Bu$^t$); D-Ser(O-$R_1$) where $R_1$ is a sugar moiety; an aliphatic D-amino acid with a ($C_1$–$C_8$)alkyl or a ($C_3$–$C_6$) cycloalkyl side chain such as D-Ala, D-Abu, D-Aib, D-3Aib, D-Val, D-Nva, D-Leu, D-Ile, D-Tle, D-Nle, D-Hol, D-Npg, D-CPa, D-Cpa, D-Cba or D-Cha; an aromatic D-amino acid such as D-Phe, D-Tyr, D-Trp, D-Nal, D-1Nal, D-diphenyl-Ala, D-anthryl-Ala, D-phenanthryl-Ala, D-benzhydryl-Ala, D-fluorenyl-Ala, D-Bal, D-Pal or D-Qal, where D-Phe and D-Trp may be substituted by one or more halogens, ($C_1$–$C_4$) alkyl, ($C_1$–$C_4$)alkoxy, nitro or trifluoromethyl groups; D-cyclohexadienyl-Gly; D-perhydronaphthyl-Ala; D-perhydrodiphenyl-Ala; or a basic L- or D-amino acid such as Arg, HArg, Orn, Lys, HLys, Cit, HCit, APhe or ACha, where Arg and HArg may be N-substituted by a ($C_1$–$C_6$)alkyl or ($C_3$–$C_6$)cycloalkyl group on one or both nitrogen atoms, and where Orn, Lys, HLys, APhe and ACha may be N-substituted by one or two ($C_1$–$C_6$) alkyl or ($C_3$–$C_6$)cycloalkyl groups, or by a nicotinoyl, isonicotinoyl, 6-methyl-nicotinoyl, glycyl-nicotinoyl, nicotinyl-azaglycyl, furyl, glycyl-furyl, furyl-azaglycyl, pyrazinyl, pyrazinyl-carbonyl, picolinoyl, 6-methyl-picolinoyl, shikimyl, shikimyl-glycyl, Fmoc or Boc group;

Npg may be N-alpha-substituted by a ($C_1$–$C_4$)alkyl group which may be substituted by one or several fluorine atoms;

A7 is a basic L- or D-amino acid such as Arg, HArg, Orn, Lys, HLys, Cit, HCit, APhe or ACha, where Arg and HArg may be N-substituted by a ($C_1$–$C_6$)alkyl or ($C_3$–$C_6$)cycloalkyl group on one or both nitrogen atoms, and where Orn, Lys, HLys, APhe and ACha may be N-substituted by one or two ($C_1$–$C_6$)alkyl or ($C_3$–$C_6$)cycloalkyl groups, or by a nicotinoyl, isonicotinoyl, 6-methyl-nicotinoyl, glycyl-nicotinoyl, nicotinyl-azaglycyl, furyl, glycyl-furyl, furyl-azaglycyl, pyrazinyl, pyrazinyl-carbonyl, picolinoyl, 6-methyl-picolinoyl, shikimyl, shikimyl-glycyl, Fmoc or Boc group;

Z is GlyNH2 or $D\text{-}AlaNH_2$;

as well as their pharmaceutically acceptable salts.

Among the peptide analogues of formula (IIa), those of the formula (SEQ ID NO: 4):

pGlu-His-A3-Ser-Tyr-A6-HAA-Arg-Pro-Z (IIa)

in which:

A3 and HAA are as defined for (IIa);

A6 is Gly; an aliphatic D-amino acid with a ($C_1$–$C_8$)alkyl side chain; or an aromatic D-amino acid;

Z is $GlyNH_2$ or a group —$NHC_2H_5$;

and their pharmaceutically acceptable salts, are especially preferred.

Among the peptide analogues of formula (IIIa), those where A3 is Trp are preferred; among the latter, those where HAA is Npg which may be N-alpha-methylated, are especially preferred.

Among the peptides of formula (IIb), those of the formula (SEQ ID NO: 5):

N-Ac-D-Nal-D-pClPhe-D-Pal-Ser-A5-A6-HAA-A7-Pro-D-$AlaNH_2$ (IIIb)

in which:

A5 and A7 are as defined above for (IIb);

A6 is Gly or a basic L- or D-amino acid;

HAA is as defined for (IIb);

and their pharmaceutically acceptable salts, are especially preferred.

Among the peptide analogues of formula (IIIb), those where HAA is Npg which ay be N-alpha-methylated, are preferred.

Examples of the salts with pharmaceutically acceptable acids are those with mineral acids, such as for example the hydrochloride, hydrobromide, sulfate, phosphate, borate, hydrogensulfate, dihydrogenphosphate or nitrate, and those with organic acids, such as for example the acetate, oxalate, tartrate, succinate, maleate, fumarate, gluconate, citrate, pamoate, malate, ascorbate, benzoate, p-toluenesulfonate or naphtalenesulfonate.

Examples of the salts with pharmaceutically acceptable bases are those with alkali or alkaline earth metals such as sodium, potassium, calcium or magnesium, and those with organic bases such as amines, trometamol, N-methylglutamine, and the like.

The peptides according to the present invention can be prepared by the well-known techniques of peptide chemistry such as for example peptide synthesis in solution or solid phase peptide synthesis. In general, these techniques involve the stepwise addition of one or more amino acids—which may be suitably protected—to a forming peptide chain.

Preferably, the peptides according to the invention are synthesized using stepwise solid phase synthesis (1,2) with N-α-Fmoc protection. For example, the peptides are assembled on a 4-methylbenzylhydrylamine resin (Peninsula Laboratories, UK) or on an aminomethyl resin (Peninsula Laboratories, UK). The C-terminal proline is introduced as 4-(Boc-Prolyloxymethyl)phenyl acetic acid. Subsequent removal of the Boc protecting group is achieved with trifluoroacetic acid followed by dichloromethane and dimethylformamide (DMF) washing as well as diisopropylethylamine neutralization. It is also possible to use a "Rink" resin (4-(2',4'-dimethoxyphenyl)-Fmoc-aminomethylphenoxy resin) using Fmoc strategy of synthesis (2).

The synthesis comprises assembling, cleavage and purification steps, as described below:

I. Assembling

For all the peptides the following deprotection/coupling procedure is used:

1—DMF washing (3 times—1 min.)

2—Piperidine 25% in DMF (1 min.)

3—Piperidine 25% in DMF (twice—15 min.)

4—DMF washing (7 times—1 min.)

For each step 15 ml of solvent per gram of peptide resin are used.

Coupling of all amino acid (three fold excess) is performed in DMF in the presence of BOP, Hobt and DIEA according to the method described by Le-Nguyen et al. (3). Each coupling step is controlled for completion by the ninhydrine test, as set forth in reference (4), and double coupling is performed if necessary. If, after the second coupling the test still remains positive, the resin is acetylated (acetic acid anhydride, 10 fold excess and DIEA).

Generally, a trifluoroacetic acid (TFA) treatment is performed prior to the deprotection/cleavage step.

II. Cleavage

The peptides are cleaved from the resin and fully deprotected by a treatment with either liquid hydrogen fluoride (HF) or TFA. 10 ml of HF or TFA per gram of peptide resin are used classically at 0° C. for 45 min. or 2.5 hours, respectively, in the presence of p-cresol and ethanedithiol (for tryptophan-containing peptides) as scavengers.

After evaporation of the HF, the crude reaction mixture is washed with diethyl ether, dissolved in TFA, precipitated with diethyl ether and dried under reduced pressure.

If need be, prior to HF deprotection the peptide is cleaved from the resin and subsequently amidated by a treatment with ethylamine (5 ml ethylamine per gram of petpide resin, −78° C., 20 hours).

When a benzyl group is present in the final product, TFA is used (10 ml per gram of peptide resin, 0° C., 2,5 hours) for the final cleavage/deprotection.

The composition of the TFA cleavage mixture in v % is the following:

TFA: 83.3%
Ethanedithiol: 2.1%
Thioanisol: 4.2%
Water: 4.2%
Phenol: 6.2[{]ps

After filtration of the resin, the peptide is precipitated from the reaction mixture by addition of a large amount of diethylether. After several washings with diethylether crude peptide is dried under reduced pressure.

III. Purification

All the peptides are purified by reverse phase liquid chromatography.

The general procedure of purification is identical for each peptide; however the gradient of organic solvent is adjusted depending on the initial retention time of the peptide.

General conditions of purification:

Equipment: KRONWALD SPERATIONSTECHNIK, Medium Pressure liquid chromatography system (Germany) equipped with Glass column.

Stationnary phase: silica Bondapack C18 (Waters) 15–25 μm, 100 A

Size of column: 40×340 mm

Elution conditions: Mobile phase:

Eluant A: 0.1% TFA in water

Eluant B: $CH_3CN$/A 60/40 (volume)

Temperature: Room

Flow rate: 40 ml

Detection: UV 210 nm

Fractionning: 5 ml per fraction

All fractions containing the target compound are individually analyzed by analytical HPLC. The fractions with a purity higher than 95% are pooled and freeze-dried. In case the requested purity is not reached after the first purification step, a second purification step and, if need be, a third purification step are performed. The conditions of purification for the second and third steps are similar as those described above except that the slope of the gradient is modified in order to increase the resolution.

After lyophilisation, all purified peptides are present as their trifluoroacetate salt. The final powder corresponding to each peptide is controlled by analytical HPLC. The structure of each compound is also assessed by mass spectral analysis and the net peptide content is determinated by UV absorption.

The peptides according to the present invention have a potent affinity for the LH-RH receptors.

This affinity has been determined according to the following method:

Pituitaries from female Sprague Dawley rats were removed and homogenized with a Potter homogenizer in a 25 mM HEPES buffer (pH 7.4) containing 0.32 M sucrose, 100 $\mu$g/l PMSF (phenylmethylsulfonylfluoride), 5.6 U/l aprotinin and 10 000 U/l bacitracin. The homogenates were centrifuged at 700 g for 10 minutes and the supernatants were further centrifuged at 12,500 g for 30 minutes. The pellets were homogenized and centrifuged as described above, but in the same buffer without sucrose.

All homogenization, centrifugation and subsequent incubation steps were carried out at 4° C.

Aliquots of membrane fractions were incubated for 2 hours in duplicate with increasing concentrations of test compounds in the presence of 20 to 70 pM of [$^{125}$I]-buserelin (between 1000 and 2000 Ci/mmol depending on ligand batches). The assay was terminated by filtration under suction (Brandel 96-well harvester) through Whatman GF/B glass fiber filters. After repeated washes, filters were placed in counting vials with scintillation cocktail to measure the radioactivity of $^{125}$I. For each experiment, curve-fitting of residual specific binding against concentrations of test compound gave the 50% inhibitory concentration ($IC_{50}$). Each compound was tested in at least 4 experiments.

This LH-RH receptor assay was characterized by 4 saturation experiments using increasing concentration of [$^{125}$I]-buserelin in the absence or presence of 1 $\mu$M unlabelled buserelin for non specific binding determination. Specific binding data were analysed according to Scatchard's method. At equilibrium (2 hours of incubation), the dissociation constant (Kd) and the number of binding sites for [$^{125}$I]-buserelin were respectively equal to 88±6 pM and 15.6±2.9 pM.

For each test compound, the inhibitory constant (Ki) was calculated from its $IC_{50}$ according to the Cheng and Prussof's equation: $Ki=IC_{50}/(1+[radioligand]/Kd)$. Ki were then transformed into pKi(=−log Ki) for final expression of affinity scales.

The natural ligand, LH-RH itself, displays a strong affinity with experimental $IC_{50}$ in the 10 nM range, i.e., a pKi equal to about 8.

So-called superagonists like buserelin, leuprorelin, tryptorelin, histrelin or deslorelin and antagonists like antide show an even stronger binding to LH-RH receptors with $IC_{50}$ in the subnanomolar range, i.e. pKi>9.

The affinity of test peptides of the invention for the LH-RH receptors is given in Table 1 below:

TABLE 1

Affinity for LH-RH receptors

| Compound | pKi (n) |
|---|---|
| Example 1 | 8.83 (3) |
| Example 2 | 9.61 (3) |
| Example 3 | 9.57 (3) |
| Example 4 | 10.01 (3) |
| Example 5 | 8.86 (3) |
| Example 6 | 9.33 (3) |
| Example 7 | 8.20 (3) |
| Example 8 | 8.73 (3) |
| Example 9 | 8.63 (3) |
| Example 10 | 9.64 (3) |
| Example 11 | 9.34 (3) |
| Example 12 | 9.79 (4) |
| Example 13 | 8.97 (3) |
| Example 14 | 9.50 (3) |
| Example 15 | 9.23 (3) |
| Example 16 | 10.17 (3) |
| Example 17 | 9.72 (3) |
| Example 18 | 10.07 (3) |
| Example 19 | 10.11 (3) |
| LH-RH | 8.04 (4) |
| Goserelin | 8.58 (4) |
| Antide | 9.16 (12) |
| Leuprorelin | 9.33 (4) |
| Buserelin | 9.35 (108) |
| Tryptorelin | 9.85 (4) |
| Deslorelin | 9.90 (4) |
| Histrelin | 9.98 (4) |

(n): number of determinations

The peptides according to the general formula (IIa) exert an agonist activity upon the LH-RH receptors in vivo, resulting in the stimulation of LH secretion by the pituitary, which, in males, stimulates the secretion of testosterone by the testis.

Adult male Sprague-Dawley rats received a subcutaneous injection of various doses of LH-RH, tryptorelin or leuprorelin, or their respective counterpart with $Npg^7$ replacing $Leu^7$: example 1 ([$Npg^7$]-LH-RH), example 6 ([$Npg^7$]-leuprorelin) or example 11 ([$Npg^7$]-tryptorelin), dissolved in phosphate-buffered saline (PBS). Two hours later, blood samples were drawn for total plasma testosterone determination by direct radioimmunoassay (Immunotech). Example 1 was a little more than twice as active as LH-RH itself, and the other compounds behaved like so-called <<superagonists>> by inducing a stronger stimulation of testosterone secretion at much lower doses (logarithmic x axis) than LH-RH (FIG. 1; 8 animals per point). At 20 ng/kg, the secretion of testosterone was equally maximally stimulated by the four superagonists (exponential y axis scale), but at 10 ng/kg, examples 6 and 11 were a little more than twice as active as leuprorelin and tryptorelin, respectively.

At this intermediate dose of 10 ng/kg, several examples with $Npg^7$ or $Ada^7$ in place of $Leu^7$ according to the invention were screened for agonistic activity (Tables 2 and 3). When available from Bachem (France) or Sigma (France), the corresponding standard agonist with $Leu^7$ was tested for comparison. In all the six instances, both $Npg^7$- and $Ada^7$-modified examples were more active, by a slight or wide margin depending on the $Leu^7$ counterpart compound (Table 2). In two cases, the $Ada^7$ replacement was more favorable than $Npg^7$ (examples 27 and 28). Conversely, $Npg^7$ led to more potent agonists than $Ada^7$ in two other structures (examples 6 and 11).

Those findings illustrate that increasing the overall hydrophobicity of the amino-acid in position 7 of LH-RH analogues is a general mean to achieve a greater potency in vivo. Depending on the rest of the molecule, other characteristics of the side chain in position 7, such as steric hindrance, modulate the resulting gain in activity.

An increase in hydrophobicity, as exemplified with $Npg^7$, was compatible with several changes in positions 3 and 6 to give several agonists in a range of potency similar to that of leuprorelin or tryptorelin (examples 5, 9, 13, 20, 21, 22 or 25; Tables 2 and 3). N-methylation of $Npg^7$ was also compatible with a very strong agonistic activity (example 23; Table 3).

TABLE 2

Stimulation of testosterone secretion

| Compound | Dose (ng/kg) | Total plasma testosterone (nmol/l) | n |
|---|---|---|---|
| Vehicle (PBS) | — | 2.7 ± 0.3 | 46 |
| [D-$Ala^6$]-LH-RH | 10 | 6.4 ± 1.9* | 8 |
| Example 3 | 10 | 16.7 ± 1.9*** | 8 |
| [D-$Ala^6$, $Pro^9$NEt]-LH-RH | 10 | 30.6 ± 7.2*** | 16 |
| Example 4 | 10 | 33.8 ± 5.8*** | 16 |
| Example 28 | 10 | 44.9 ± 6.0*** | 16 |
| [D-$Phe^6$, $Pro^9$NEt]-LH-RH | 10 | 16.7 ± 4.3*** | 16 |
| Example 10 | 10 | 23.5 ± 4.0*** | 16 |
| Example 27 | 10 | 28.0 ± 4.1*** | 16 |
| Leuprorelin | 10 | 33.5 ± 3.5*** | 22 |
| Example 6 | 10 | 48.6 ± 4.3*** | 22 |
| Example 29 | 10 | 36.2 ± 4.5*** | 16 |
| Tryptorelin | 10 | 20.3 ± 2.5*** | 22 |
| Example 11 | 10 | 30.8 ± 3.5*** | 22 |
| Example 30 | 10 | 24.8 ± 4.1*** | 15 |
| Deslorelin | 10 | 11.8 ± 3.5** | 6 |
| Example 12 | 10 | 20.5 ± 5.2*** | 6 |
| Example 5 | 10 | 21.2 ± 6.6** | 6 |
| Example 9 | 10 | 30.9 ± 3.6*** | 8 |
| Example 13 | 10 | 22.9 ± 4.2*** | 6 |

*$p < 0.05$;
**$p < 0.01$;
***$p < 0.001$ compared to vehicle alone
n: number of animals

TABLE 3

Stimulation of testosterone secretion

| Compound | Dose (ng/kg) | Total plasma testosterone (nmol/l) | n |
|---|---|---|---|
| Vehicle (PBS) | — | 4.3 ± 1.2 | 16 |
| Example 20 | 10 | 24.9 ± 5.0** | 8 |
| Example 21 | 10 | 32.4 ± 7.0** | 8 |
| Example 22 | 10 | 34.8 ± 4.5*** | 8 |
| Example 23 | 10 | 49.4 ± 4.6*** | 8 |
| Example 24 | 10 | 14.3 ± 4.3* | 8 |
| Example 25 | 10 | 27.3 ± 6.9** | 8 |
| Example 26 | 10 | 12.2 ± 2.7 | 8 |

*$p < 0.05$; $p < 0.01$; *$p < 0.001$ compared to vehicle alone
n: number of animals In conclusion, examples 6 and 23 on the one hand, and example 28 on the other hand, are the best examples to date of more potent LH-RH agonists than current therapeutic LH-RH analogues, obtained by increasing the hydrophobicity of the amino acid in position 7, respectively with Npg or Ada.

The peptides according to the general formula (IIb) exert an antagonistic activity upon the LH-RH receptors in vivo, resulting in the inhibition of ovulation in the female.

Adult female Wistar rats are first monitored for normal estrous cyclicity by daily vaginal smears. After at least 2 regular 4-day cycles, they received by subcutaneous injection either the vehicle alone (0.5 ml of a mixture of propylene-glycol and water:20/80 vol/vol), or the LH-RH antagonist according to the formula (IIb) dissolved in this vehicle, around 2:00 PM on the day of proestrus. All but one vehicle-treated animals ovulated spontaneously as demonstrated by the recovery of numerous ovocytes in the oviducts the following morning.

When effective, LH-RH antagonists totally block ovulation. Antide, a commercially available standard LH-RH antagonist (from Bachem, France) showed a dose-related inhibition of ovulation (Table 4). Semi-logarithmic regression analysis gave a 50% inhibitory dose ($ID_{50}$) equal to 0.99 $\mu$g/rat. When $Leu^7$ was replaced by $Npg^7$ in the structure of antide (example 15), the inhibitory potency was markedly increased at 0.5 and 0.25 $\mu$g/rat, resulting in an $ID_{50}$ of 0.26 $\mu$g/rat. Variations in basic amino acids in positions 6 and 8 were compatible with $Npg^7$ to give antagonists more potent than antide, as seen with the maximal or sub-maximal activity of examples 16, 17, 18 or 19 at the dose of 1 $\mu$g/rat (Table 4). Example 17 was especially active, but its effects were not related to the dose in the dose range studied. Therefore, introduction of an hydrophobic amino acid in position 7 is favorable to achieve stronger LH-RH antagonistic properties, as best examplified to date by the 4-fold increase in the antiovulatory potency of antide by replacement of $Leu^7$ by $Npg^7$ (example 15).

TABLE 4 inhibition of ovulation

| Treatment | Dose ($\mu$g/rat) | Number of ovulating females/ total number of treated females | % of inhibition |
|---|---|---|---|
| Vehicle | — | 38/39 | — |
| Antide | 10 | 0/8 | 100% |
| | 5 | 0/11 | 100% |
| | 2.5 | 2/6 | 67% |
| | 1 | 5/16 | 69% |
| | 0.5 | 4/5 | 20% |
| [$Npg^7$]-antide | 1 | 1/5 | 80% |
| (Example 15) | 0.5 | 0/5 | 100% |
| | 0.25 | 4/10 | 60% |
| | 0.1 | 5/5 | 0% |
| Example 16 | 1 | 0/5 | 100% |
| | 0.25 | 4/5 | 20% |
| Example 17 | 1 | 0/12 | 100% |
| | 0.75 | 0/7 | 100% |
| | 0.5 | 4/7 | 43% |
| | 0.25 | 1/5 | 80% |
| Example 18 | 1 | 1/5 | 80% |
| | 0.25 | 4/5 | 20% |
| Example 19 | 1 | 0/5 | 100% |
| | 0.25 | 3/5 | 40% |

In conclusion of both agonistic and antagonistic studies in vivo, it has been shown that replacement of $Leu^7$ by a more hydrophobic non aromatic amino acid, such as Npg or Ada, systematically increased the potency of existing analogues. Furthermore, closely related analogues having an hydrophobic amino acid in position 7 without direct $Leu^7$ counterpart for comparison, often displayed interesting levels of activity per se.

Therefore, the use of Npg, Ada or any other hydrophobic amino acid in position 7 of an LH-RH analogue sequence corresponding to the definition of general formula (I) is claimed as a general feature to obtain new LH-RH agonists or antagonists with high or enhanced potency in vivo.

No sign of toxicity is observed with the peptides of the invention at pharmaceutically active doses.

Thus, the peptides of the invention and their pharmaceutically acceptable salts may be used in the treatment or prevention of various complaints or diseases wherein a LH-RH agonist or antagonist activity is required.

The main target of LH-RH analogues is the pituitary gland, but direct actions have been reported on the gonads themselves (testis and ovary), on the thymus and some lymphoid cell lines, on mast cells and on breast, prostate or pancreatic tumors.

LH-RH agonists according to formula (IIa) exert on any LH-RH sensitive target, either a stimulatory activity by short-term acute or pulsatile administrations, or an inhibitory effect by repeated or continuous administrations that induce the desensitization and the down-regulation of LH-RH receptors. In the case of the hypothalamo-pituitary-gonadal axis, prolonged administration results in a so-called "chemical" castration.

LH-RH antagonists according to formula (IIb) exert primarily an inhibitory effect on any LH-RH-sensitive target, but are also useful in obtaining or planning a rebound stimulatory release of LH and FSH when treatment is discontinued.

Due to this ambivalent potential of both LH-RH agonists and antagonists, all analogues according to formula (I) can find an appropriate therapeutic use in humans as well as in animals, depending on doses, treatment regimens and routes of administration, in reproductive endocrinology and in the treatment or prevention of sex hormone-dependent benign or malignant tumors, alone or in combination with other hormonal or antitumoral agents. LH-RH sensitive sex hormone-independent benign or malignant tumors can also regress upon treatment with LH-RH analogues according to formula (I), alone or in combination with antitumoral agents. Immune mechanisms can also be modified by LH-RH analogues according to formula (I), alone or in combination with immuno-modulating or -suppresive agents such as glucocorticoids, cyclosporin, rapamycin, tacrolimus, their derivatives, and the like. The LH-RH analogues according to the invention are therefore very valuable in the treatment and prevention of autoimmune diseases, graft rejection or atopic diseases, and in the treatment of benign or malignant lymphoproliferative disorders.

LH-RH analogues according to formula (I) are especially useful, alone or in combination with sex steroids or gonadotrophins, in the inhibition, planning and triggering of ovulation in in vitro fertilization programs, and in the treatment of male and female infertility or hypogonadic states. Conversely, they can also be used in male or female contraception or treatment of hypergonadic states, alone or in combination with sex steroids or gonadotrophins. This applies to men and women, but also to wild or domestic animals in uses such as improvement or control of reproductive performance, or as a tool to optimize breeding strategies.

LH-RH analogues according to formula (I) are also especially useful in men to treat advanced prostate cancer, but can also be used as a first line therapy in this indication and in benign prostatic hypertrophy, alone or in combination with inhibitors of androgen action, i.e. antiandrogens such as cyproterone acetate, osaterone acetate, chlormadinone acetate, flutamide, nilutamide or bicalutamide and the like, or 5$\alpha$-reductase inhibitors such as finasteride, epristeride or turosteride and the like, or $C_{17-20}$ lyase inhibitors such as abiraterone and the like.

LH-RH analogues according to formula (I) are also especially useful in the treatment or prevention of breast cancer in women and in men, especially estrogen receptor positive tumors, alone or in combination with antiestrogens such as tamoxifen, raloxifen or droloxifen and the like, or with aromatase inhibitors such as atamestane, formestane, letrozole, anastrozole and the like, or with $C_{17-20}$ lyase inhibitors such as abiraterone and the like, but also of certain estrogen receptor negative tumors that respond to the direct effects of LH-RH analogues or indirectly to their gonadal suppressive activity.

Other gynecological conditions, such as endometrial hyperplasia, leiomyoma, adenomyoma, endometriosis, polycystic ovary syndrome, hirsutism and benign breast disease (pain, cysts or fibrosis), can also be prevented by or benefit from treatment with the LH-RH analogues according to formula (I), alone or in combination with antiestrogens (cited above), progestins such as cyproterone acetate, osaterone acetate, chlormadinone acetate, nomegestrol acetate, promegestone, demegestone, trimegestone and the like, or their contraceptive or post-menopausal replacement combination formulations with estrogens such as estradiol or ethynylestradiol. The peptides of the invention can also interfere with gestation by inducing abortion or by triggering labor, alone or in combination with estrogens (cited above), antiprogestins such as mifepristone or prostaglandin analogs such as sulprostone.

Similar indications can be encountered in veterinary medicine for male or female domestic or wild animals that may require the use of LH-RH analogues according to formula (I).

Another aspect of the present invention is therefore pharmaceutical compositions containing an effective amount of at least one peptide of formula (I) or a pharmaceutically acceptable salt thereof, alone or mixed with suitable pharmaceutical excipients.

A further aspect of the invention relates to a method of treating and/or preventing the above diseases which comprises administering to patients or animals in need thereof a therapeutically effective amount of a peptide of formula (I) or a pharmaceutically acceptable salt thereof.

A further aspect of the invention relates to the use of the peptides of formula (IIa), or of their pharmaceutically acceptable salts, for the preparation of a medicament having LH-RH agonist activity. Also within the scope of the invention is the use of the peptides of formula (IIb), or of their pharmaceutically acceptable salts, for the preparation of a medicament having LH-RH antagonist activity.

The peptides of the invention are preferentially administered by parenteral administration, although oral formulations are also effective provided that the dosage is appropriately increased.

Preferred delivery systems for LH-RH agonists of formula (IIa) in long term pituitary-gonadal suppressive indications are slow-release implantable devices, or injectable biodegradable polymeric micro- or nano-particles or -capsules, or micro- or nano-emulsions, with unit doses of the peptides or of their appropriate salts ranging from 1 mg to 100 mg per human patient for a duration of action ranging from 1 month to 1 year. Long term administration of LH-RH antagonists of formula (IIb) will generally require higher dosages in the same slow-release formulations, ranging from 10 mg to 1 g for 1 week to 1 year of activity. Animal doses will be adapted on a body weight basis depending on the wild or domestic species to be treated either by LH-RH agonists or antagonists according to formula (I).

All other means of parenteral administration are suited for immediate, delayed or planned delivery of the peptides of the invention: subcutaneous, intramuscular, intravenous, intragonadal or intratumoral needle bolus injections, or prolonged continuous, pulsatile or planned perfusions or microinfusions using the appropriate pump technology; gas-propelled subcutaneous microinjection; vaginal creams, gels or pessaries; rectal enemas or suppositories; transdermal creams, gels, lotions, solutions, patches or iontophoretic devices; nasal spray or dry powder inhalation device; ophtalmic solutions, gels, creams or contact lenses; pulmonary inhalation of micro- or nano-particles or droplets generated manually or with an appropriate pulverization or nebulization device.

The unit dose of these parenteral administrations will range in humans from 0.001 mg to 10 mg/day for LH-RH agonists of formula (IIa) and from 0.01 to 100 mg/day for LH-RH antagonists of formula (IIb), one to 16 times per day (in the case of pulsatile administration).

Oral administration of peptides according to the invention is preferentially effected using gastro-resistant and delayed enteric or colonic release formulations which can be coated pills or tablets containing two or more components, hardened gelatin capules, special polymeric macro-, micro- or nano-beads containing them, or any device designed to protect them from gastrointestinal degradation and to release them when needed. All other formulations to be taken orally such as solutions, suspensions, syrups, gels and the like, or lingual, sublingual or chewable formulations are suited provided that the dosage is increased.

Overall, effective oral treatment may be achieved with any of the above formulations with unit doses of peptides of formula (I) ranging from 1 mg to 1 g per human patient, from one to 16 times per day (in the case of pulsatile administration).

All the above-mentioned oral or parenteral formulations of the peptides according to the invention and their pharmaceutical acceptable salts may contain one or several pharmaceutically appropriate excipients, one or several inhibitors of proteases, and one or several absorption enhancers as needed by the specific route of administration.

Raw powder of pure peptides according to the invention or their pharmaceutically acceptable salts can also be used, especially in the lyophilized form for fast sublingual application.

BRIEF DESCRIPTION

FIG. 1: Stimulation of testosterone in adult male Sprague-Dawley rats in vivo by LH-RH, ([$Npg^7$]-LII-RII (example 1), leuprorelin, ([$Npg^7$]-leuprorelin (example 6), tryptorelin, and ([$Npg^7$]-tryptorelin (example 11).

The invention will now be described with reference to the following examples, which are not intended to limit the invention in any respect. In these examples, the starting materials used were either commercially available or synthetized, as mentioned below:

Fmoc-Glu-OH, Fmoc-Tyr(OBut)-OH, Fmoc-Trp-OH and Fmoc-His(Trt) were purchased from Propeptide (France).

Fmoc-β-Nal-OH and Fmoc-pClPhe were synthesized as racemates. These amino acids and their corresponding acetyl ethylesters were enzymatically resolved using subtilisin (5);

Other Fmoc protected amino-acids were purchased from Bachem (Switzerland), Novabiochem (Switzerland), American Peptide C° (USA) or Neosystem (France).

Adamantylalanine was synthesized as described by Kim Quang Do et al (6).

EXAMPLE 1 pGlu-His-Trp-Ser-Tyr-Gly-Npg-Arg-Pro-Gly-$NH_2$ (SEQ ID NO: 9)

Example 1 was synthesized on a Rink resin using a Fmoc strategy as mentioned above in the general synthesis of the invention peptides. Cleavage was carried out with TFA in the presence of scavengers.

Purification was carried out using a linear gradient of from 10 to 40% of eluent B ($CH_3CN$/0.1% TFA 60/40 v/v) over 30 min.

68 mg (approximate yield 24%) of purified material were obtained.

Mass spectral analysis—$ES^+$ mode:

expected: 1195.3 found: 1195.7.

net peptide content 73.9%; purity 97.2%; retention time 16.4 min.

EXAMPLE 2 pGlu-His-Trp-Ser-Tyr-Gly-Npg-Arg-Pro-NEt (SEQ ID NO: 10)

The synthesis was carried out on Boc-Pro-PAM resin. The second amino acid, arginine, was also incorporated via a Boc strategy. The subsequent amino acids were incorporated via a Fmoc strategy. After coupling of the N-terminal amino acid, the peptide was cleaved from the resin and converted into ethylamide by aminolysis using ethylamine (5 ml of ethylamine per gram of peptide resin for 20 hours, −78° C.).

After cleavage the protected peptide was extracted with methanol, dried and deprotected with HF as described.

Purification was carried out using a linear gradient of from 10 to 60% of eluent B over 30 min. 15 mg (approximate yield 8%) of purified material were obtained.

Mass spectral analysis—$ES^+$ mode:

expected: 1166.3 found: 1166.8.

net peptide content 72.7%; purity 95.0%; retention time 15.1 min.

EXAMPLE 3 pGlu-His-Trp-Ser-Tyr-D-Ala-Npg-Arg-Pro-Gly-$NH_2$ (SEQ ID NO:11)

Assembling and cleavage of the peptide were carried out as described for Example 1.

Purification was carried out using a linear gradient of from 10 to 50% of eluent B over 30 min.

66 mg (approximate yield 27%) of purified material were obtained.

Mass spectral analysis—$ES^+$ mode:

expected: 1209.4 found: 1209.5.

net peptide content 72.6%; purity 95.2%; retention time 14.5 min.

EXAMPLE 4 pGlu-His-Trp-Ser-Tyr-D-Ala-Npg-Arg-Pro-NEt (SEQ ID NO:12)

Assembling and cleavage of the peptide were carried out as described for Example 2.

Purification was carried out using a linear gradient of from 10 to 60% of eluent B over 30 min.

8 mg (approximate yield 7%) of purified material were obtained.

Mass spectral analysis—$ES^+$ mode:

expected: 1180.3 found: 1181.0 net peptide content 69.5%; purity 96.9%; retention time 17.7 min.

EXAMPLE 5 pGlu-His-Trp-Ser-Tyr-D-Leu-Npg-Arg-Pro-Gly-$NH_2$ (SEQ ID NO:13)

Assembling and cleavage of the peptide were carried out as described for Example 2.

Purification was carried out using a linear gradient of from 15 to 50% of eluent B over 30 min.

123 mg (approximate yield 36%) of purified material were obtained.

Mass spectral analysis—$ES^+$ mode:

expected: 1251.4 found: 1251.9 net peptide content 71.7%; purity 95.7%; retention time 13.9 min.

EXAMPLE 6 pGlu-His-Trp-Ser-Tyr-D-Leu-Npg-Arg-Pro-NEt (SEQ ID NO: 14)

Assembling and cleavage of the peptide were carried out as described for Example 2.

Purification was carried out in two steps, the first one using a linear gradient of from 15 to 50% of eluent B over 30 min., and the second one using a linear gradient of from 15 to 40% of eluent B over 30 min.

49 mg (approximate yield 20%) of purified material were obtained.

Mass spectral analysis—$ES^+$ mode:

expected: 1222.4 found: 1223.6 ($MH^+$)

net peptide content 73.6%; purity 95.3%; retention time 14.6 min.

EXAMPLE 7 pGlu-His-Trp-Ser-Tyr-D-Npg-Npg-Arg-Pro-Gly-$NH_2$ (SEQ ID NO:15)

Assembling and cleavage of the peptide were carried out as described for Example 1.

Purification was carried out in two steps, the first one using a linear gradient of from 30 to 60% of eluent B over 30 min., and the second one using a linear gradient of from 25 to 60% of eluent B over 30 min.

13 mg (approximate yield 4%) of purified material were obtained.

Mass spectral analysis—$ES^+$ mode:

expected: 1265.5 found 1266.0 net peptide content 71.1%; purity 97.8%; retention time 15.1 min.

EXAMPLE 8 pGlu-His-Trp-Ser-Tyr-D-Npg-Npg-Arg-Pro-NEt (SEQ ID NO: 16)

Assembling and cleavage of the peptide were carried out as described for Example 2.

Purification was carried out using a linear gradient of from 20 to 80% of eluent B over 30 min.

13 mg (approximate yield 4%) of purified material were obtained.

Mass spectral analysis—$ES^+$ mode:

expected: 1236.4 found: 1237.5 ($MH^+$)

net peptide content 68.5%; purity 96.2%; retention time 13.9 min.

EXAMPLE 9 pGlu-His-Trp-Ser-Tyr-D-Phe-Npg-Arg-Pro-Gly-$NH_2$ (SEQ ID NO:17)

The synthesis was carried out as described for example 1.

Purification was carried out using a linear gradient of from 25 to 80% of eluent B over 30 min.

61 mg (approximate yield 16%) of purified material were obtained.

Mass spectral analysis—$ES^+$ mode:

expected: 1285.5 found: 1286.2 ($MH^+$)

net peptide content 71.8%; purity 96.8%; retention time 14.9 min.

EXAMPLE 10 pGlu-His-Trp-Ser-Tyr-D-Phe-Npg-Arg-Pro-NEt (SEQ ID NO:18)

Assembling and cleavage of the peptide were carried out as described for example 2.

Purification was carried out using a linear gradient of from 20 to 80% of eluent B over 30 min.

61 mg (approximate yield 4%) of purified material were obtained.

Mass spectral analysis—$ES^+$ mode:

expected: 1256.4 found: 1257.4 ($MH^+$)

net peptide content 63.2%; purity 96.9%; retention time 13.9 min.

EXAMPLE 11 pGlu-His-Trp-Ser-Tyr-D-Trp-Npg-Arg-Pro-Gly-$NH_2$ (SEQ ID NO:19)

Assembling and cleavage of the peptide were carried out as described for example 1.

Purification was carried out using a linear grandient of from 20 to 80% of eluent over 30 min.

22 mg (approximate yield 7%) of purified material were obtained.

Mass spectral analysis—$ES^+$ mode:

expected: 1324.5 found: 1325.5 ($MH^+$)

net peptide content 71.6%; purity 97.1%; retention time 13.1 min.

EXAMPLE 12 pGlu-His-Trp-Ser-Tyr-D-Trp-Npg-Arg-Pro-NEt (SEQ ID NO:20)

Assembling and cleavage of the peptide were carried out as described for example 1.

Purification was carried out using a linear gradient of from 20 to 80% of eluent B over 30 min.

10 mg (approximate yield 5%) of purified material were obtained.

Mass spectral analysis—$ES^+$ mode:

expected: 1295.4 found: 1296.3 ($MH^+$)

net peptide content 71.3%; purity 98.4%; retention time 13.8 min.

EXAMPLE 13 pGlu-His-Trp-Ser-Tyr-D-Nal-Npg-Arg-Pro-Gly-$NH_2$ (SEQ ID NO:21)

Assembling and cleavage of the peptide were carried out as described for example 1.

Purification was carried out using a linear gradient of from 15 to 75% of eluent B over 30 min.

205 mg (approximate yield 50%) of purified material were obtained.

Mass spectral analysis—$ES^+$ mode:

expected: 1335.6 found: 1336.2 ($MH^+$)

net peptide content 74.8%; purity 95.6%; retention time 14.9 min.

EXAMPLE 14 pGlu-His-Trp-Ser-Tyr-D-Nal-Npg-Arg-Pro-NEt (SEQ ID NO:22)

Assembling and cleavage were carried out as described for example 2.

Purification was carried out using a linear gradient of from 25 to 50% of eluent B over 30 min.

82 mg (approximate yield 22%) of purified material were obtained.

Mass spectral analysis—$ES^+$ mode:

expected: 1306.5 found: 1307.2 ($MH^+$)

net peptide content 76.0%; purity 97.4%; retention time 15.8 min.

EXAMPLE 15

AcD-Nal-D-pClPhe-D-Pal-Ser-NicLys-D-NicLys-Npg-IprLys-Pro-D-Ala-$NH_2$ (SEQ ID NO:23)

The synthesis was carried out on a 4-methylbenzhydrylamine resin.

D-alanine and proline were introduced using a Boc strategy as described above for the general synthesis of the invention peptides. The other amino acids were incorporated via a Fmoc strategy as described above.

The synthesis was started with Boc-D-Ala-OH.

The peptides were deprotected and cleaved from the resin using HF as described above.

Purification was carried out using a linear gradient of from 15 to 70% of eluent B over 30 min.

49 mg (approximate yield 31%) of purified material were obtained.

Mass spectral analysis—$ES^+$ mode:

expected: 1605.3 found: 1605.5 net peptide content 67.6%; purity 98.3%; retention time 15.5 min.

EXAMPLE 16

AcD-Nal-D-pClPhe-D-Pal-Ser-Tyr-D-Cit-Npg-Arg-Pro-D-Ala-$NH_2$ (SEQ ID NO:24)

Assembling and cleavage of the peptide were carried out as described for example 15, arginine being introduced using a Boc strategy.

Purification was carried out using a linear gradient of from 30 to 60% of eluent B over 30 min.

16 mg (approximate yield 9%) of purified material were obtained.

Mass spectral analysis—$ES^+$ mode:

expected: 1444.9 found: 1444.6 net peptide content 67.1%; purity 97.0%; retention time 16.8 min.

EXAMPLE 17

AcD-Nal-D-pClPhe-D-Pal-Ser-Tyr-D-Cit-Npg-IprLys-Pro-D-Ala-$NH_2$ (SEQ ID NO: 25)

Assembling and cleavage of the peptide were carried out as described for Example 15.

Purification was carried out using a linear gradient of from 10 to 60% of eluent B over 30 min.

55 mg (approximate yield 29%) of purified material were obtained.

Mass spectral analysis—$ES^+$ mode:

expected value: 1459.9 found: 1459.3 net peptide content 69.8%; purity: 96.4%; retention time 11.2 min.

EXAMPLE 18

AcD-Nal-D-pClPhe-D-Pal-Ser-Tyr-D-HCit-Npg-IprLys-Pro-D-Ala-$NH_2$ (SEQ ID NO:26)

Assembling and cleavage of the peptide were carried out as described for example 15.

Purification was carried out using a linear gradient of from 30 to 50% of eluent B over 30 min.

40 mg (approximate yield 17%) of purified material were obtained.

Mass spectral analysis—$ES^+$ mode:

expected: 1473.2 found: 1473.2 net peptide content 69.8%; purity 95.7%; retention time 15.9 min.

EXAMPLE 19

AcD-Nal-D-pClPhe-D-Pal-Ser-Tyr-D-HCit-Npg-Arg-Pro-D-Ala-$NH_2$ (SEQ ID NO: 27)

Assembling and cleavage of the peptide were carried out described for example 16.

Purification was carried out using a linear gradient of from 30 to 60% of eluent B over 30 min.

55 mg (approximate yield 21%) of purified material were obtained.

Mass spectral analysis—$ES^+$ mode:

expected: 1459.1 found: 1459.2 net peptide content 68.2%; purity 96.6%; retention time 15.7 min.

EXAMPLE 20 pGlu-His-Trp-Ser-Tyr-D-Pal-Npg-Arg-Pro-Gly-$NH_2$ (SEQ ID NO:28)

Assembling and cleavage of the peptide were carried out as described for Example 1.

Purification was carried out using a linear gradient of from 5 to 50% of eluent B over 30 min.

74 mg (approximate yield 29%) of purified material were obtained.

Mass spectral analysis—$ES^+$ mode:

expected: 1287.3 found: 1287.3 net peptide content 72.1%; purity 98.6%; retention time 12.5 min.

EXAMPLE 21 pGlu-His-Trp-Ser-Tyr-D-4Pal-Npg-Arg-Pro-Gly-$NH_2$ (SEQ ID NO:29)

Assembling and cleavage of the peptide were carried out as described for Example 1.

Purification was carried out using a linear gradient of from 10 to 30% of eluent B over 30 min.

7 mg of purified material were obtained.

Mass spectral analysis—$ES^+$ mode:

expected: 1287.3 found: 1287.2 net peptide content 64.3%; purity 98.4%; retention time 12.2 min.

EXAMPLE 22 pGlu-His-Trp-Ser-Tyr-D-HPhe-Npg-Arg-Pro-Gly-$NH_2$ (SEQ ID NO: 30)

Assembling and cleavage of the peptide were carried out as described for Example 1.

Purification was carried out using a linear gradient of from 15 to 70% of eluent B over 30 min.

94 mg (approximative yield 36%) of purified material were obtained.

Mass spectral analysis—$ES^+$ mode:

expected: 1300.3 found: 1300.2 net peptide content 74.2%; purity 97.5%; retention time 15.5 min.

EXAMPLE 23 pGlu-His-Trp-Ser-Tyr-D-Leu-MeNpg-Arg-Pro-NEt (SEQ ID NO: 31)

Assembling and cleavage of the peptide were carried out as described for Example 2.

Purification was carried out using a linear gradient of from 20 to 80% of eluent B over 30 min.

50 mg (approximate yield 17%) of purified material were obtained.

Mass spectral analysis—$ES^+$ mode expected: 1237.5 found: 1237.4 net peptide content 73.7%; purity 95.0%; retention time 16.2 min.

EXAMPLE 24 pGlu-His-1Nal-Ser-Tyr-D-Leu-Npg-Arg-Pro-NEt (SEQ ID NO:32)

Assembling and cleavage of the peptide were carried out as described for Example 2.

Purification was carried out using a linear gradient of from 10 to 70% of eluent B over 30 min.

68 mg (approximate yield 7%) of purified material were obtained.

Mass spectral analysis—$ES^+$ mode:

expected: 1234.5 found: 1234.2 net peptide content 73.3%; purity 98.5%; retention time 15.5 min.

EXAMPLE 25 pGlu-His-2Nal-Ser-Tyr-D-Leu-Npg-Arg-Pro-NEt (SEQ ID NO: 33)

Assembling and cleavage of the peptide were carried out described for example 2.

Purification was carried out using a linear gradient of from 10 to 65% of eluent B over 30 min.

17 mg (approximate yield 7%) of purified material were obtained.

Mass spectral analysis—$ES^+$ mode:

expected: 1234.5 found: 1234.2 net peptide content 71.5%; purity 98.0%; retention time 14.0 min.

EXAMPLE 26 pGlu-His-Bal-Ser-Tyr-D-Leu-Npg-Arg-Pro-NEt (SEQ ID NO: 34)

Assembling and cleavage of the peptide were carried out as described for Example 2.

Purification was carried out using a linear gradient of from 20 to 70% of eluent B over 30 min.

41 mg (approximate yield 16%) of purified material were obtained.

Mass spectral analysis—$ES^+$ mode:

expected: 1240.5 found: 1240.4 net peptide content 89.0%; purity 97.4%; retention time 15.6 min.

EXAMPLE 27 pGlu-His-Trp-Ser-Tyr-D-Phe-Ada-Arg-Pro-NEt (SEQ ID NO: 35)

Assembling and cleavage of the peptide were carried out as described for Example 2.

Purification was carried out using a linear gradient of from 15 to 50% of Eluent B over 30 min.

90 mg (approximate yield 14%) of purified material were obtained.

Mass spectral analysis—$ES^+$ mode:

expected: 1335.6 found: 1335.5 net peptide content 76.3%; purity 97.8%; retention time 17.0 min.

EXAMPLE 28 pGlu-His-Trp-Ser-Tyr-D-Ala-Ada-Arg-Pro-NEt (SEQ ID NO:36)

Assembling and cleavage of the peptide were carried out as described for Example 2.

Purification was carried out using a linear gradient of from 15 to 50% of eluent B over 30 min.

150 mg (approximate yield 24%) of purified material were obtained.

Mass spectral analysis—$ES^+$ mode expected: 1259.5 found: 1259.0 net peptide content 72.9%; purity 97.4%; retention time 14.1 min.

EXAMPLE 29 pGlu-His-Trp-Ser-Tyr-D-Leu-Ada-Arg-Pro-NEt (SEQ ID NO: 37)

Assembling and cleavage of the peptide were carried out as described for Example 2.

Purification was carried out using a linear gradient of from 15 to 70% of eluent B over 30 min.

100 mg (approximate yield 15%) of purified material were obtained.

Mass spectral analysis—$ES^+$ mode:

expected: 1301.6 found: 1301.5 net peptide content 72.7%; purity 97.3%; retention time 17.7 min.

EXAMPLE 30 pGlu-His-Trp-Ser-Tyr-D-Trp-Ada-Arg-Pro-Gly-$NH_2$ (SEQ ID NO:38)

Assembling and cleavage of the peptide were carried out as described for Example 1.

Purification was carried out using a linear gradient of from 15 to 70% of eluent B over 30 min.

30 mg (approximate yield 11%) of purified material were obtained.

Mass spectral analysis—$ES^+$ mode:

expected: 1403.6 found: 1403.2 net peptide content 82.9%; purity 95.0%; retention time 16.0 min.

REFERENCES (1) G. BARANY and R. B. MERRIFIELD (1979) The Peptides, Analysis, Synthesis, Biology, Vol. 2, Chapter 1.
(2) E. ATHERTON and R. C. SHEPPARD (1989) Solid phase peptide synthesis, IRL Press, OXFORD
(3) D. Le NGUEN, A. HEITZ and B. CASTRO (1987) J. Chem. Soc. Perkin Trans. I, 1915
(4) E. KAISER, R. L. COLESCOTT, C. D. BOSSINGER and P. I. COOK (1970) Anal. Biochem., 34, 595
(5) P. N. RAO, J. E. BURDETT Jr, J. W. CESSAD, C. M. D I NUNNO, D. M. PETERSON and H. K. KIM (1987) Int. J. Pept. Protein Res., 2, 118
(6) KIM QUANG D O, P. THANEI, M. CAVIEZEL and R. SCHWYZER (1979) Helvetica Chimica Acta, 6, 956–964

What is claimed is:

1. A peptide agonist or antagonist of LH-RH in which leucine in reference SEQ ID NO:39 is replaced by neopentylglycine or adamantylalanine, wherein neopentylglycine is unsubstituted or N-alpha substituted by a ($C_1$–$C_4$)alkyl; or a pharmaceutically acceptable salt thereof.

2. A peptide agonist or antagonist of LH-RH, of formula (I) as depicted by SEQ ID NO: 1:

A1-A2-A3-A4-A5-A6-HAA-A7-Pro-Z (1)

in which:

A1 is pGlu, D-pGlu, Sar, N-AcSar, Pro, N-AcPro, an aromatic D-amino acid or an acylated aromatic D-amino acid;

A2 is His, or an aromatic D-amino acid;

A3 is an aromatic L- or D-amino acid;

A4 is Ser, D-Ser, N-MeSer, Ser(OBu$^t$), Ser(OBzl) or Thr;

A5 is an aromatic L-amino acid or a basic L- or D-amino acid;

A6 is Gly, D-Pro, D-Ser, D-Thr, D-Cys, D-Met, D-Pen, D-(S-Me)Pen, D-(S-Et)Pen, D-Ser(OBu$^t$), D-Asp (OBu$^t$), D-Glu(OBu$^t$), D-Thr(OBu$^t$), D-Cys(OBu$^t$), D-His which is unsubstituted or substituted on the imidazole ring by a ($C_1$–$C_6$)alkyl or by a ($C_2$–$C_7$)acyl group, an aliphatic D-amino acid with a ($C_1$–$C_8$)alkyl or a ($C_3$–$C_6$)cycloalkyl side chain, an aromatic D-amino acid, D-cyclohexadienyl-Gly, D-perhydronaphthyl-Ala, D-perhydrodiphenyl-Ala, or a basic L- or D-amino acid;

HAA is Ada or Npg which is unsubstituted or N-alpha substituted by a ($C_1$–$C_4$)alkyl;

A7 is a basic L- or D-amino acid; and

Z is $GlyNH_2$, $D\text{-}AlaNH_2$, $azaGlyNH_2$, or a group —$NHR_2$ where $R_2$ is a ($C_1$–$C_4$)alkyl which is unsubstituted or substituted by one or several fluorine atoms, a ($C_3$–$C_6$)cycloalkyl or a heterocyclic radical selected from the group consisting of morpholinyl, pyrrolidinyl and piperidyl;

or a pharmaceutically acceptable salt thereof.

3. The peptide according to claim 2, in which:

A1 is pGlu, Sar or N-AcSar;

A2 is His;

A3 is Trp, Nal, or 1Nal;

A5 is an aromatic L-amino acid;

A6 is D-Pro, D-Ser, D-Thr, D-Cys, D-Met, D-Pen, D-(S-Me)Pen, D-Ser(OBu$^t$), D-His which is unsubstituted or substituted on the imidazole ring by a methyl, D-Ala, D-Leu, D-Npg, D-Cha, D-Cpa, D-Phe, D-Trp, D-Nal, D-Nal, D-Pal, D-APhe or D-HPhe;

A7 is Arg; and

Z is $GlyNH_2$, $azaGlyNH_2$ or a group —$NHR_2$;

or a pharmaceutically acceptable salt thereof.

4. The peptide according to claim 3, which is [D-Ala$^6$-Npg$^7$-Pro$^9$NHEt]LHRH, as depicted by SEQ ID NO:12.

5. The peptide according to claim 3, which is [D-Leu$^6$-Npg$^7$-Pro$^9$NHEt]LHRH, as depicted by SEQ ID NO:14.

6. The peptide according to claim 3, which is [D-Ala$^6$-Ada$^7$-Pro$^9$NHEt]LHRH, as depicted by SEQ ID NO:36.

7. The peptide according to claim 3, which is [D-Leu$^6$-N-Me-Npg$^7$-Pro$^9$NHEt]LHRH,as depicted by SEQ ID NO:31.

8. The peptide according to claim 3 wherein HAA is Npg which is unsubstituted or N-alpha substituted by a ($C_1$–$C_4$) alkyl; or a pharmaceutically acceptable salt thereof.

9. The peptide according to claim 8 wherein HAA is Npg which is N-alpha-methylated; or a pharmaceutically acceptable salt thereof.

10. The peptide according to claim 3, in which:

A1 is pGlu;

A4 is Ser;

A5 is Tyr;

A6 is D-Ser(OBu$^t$), D-Ala, D-Leu, D-Npg, D-Cha, D-Cpa, D-Phe, D-Trp, D-Nal, D-1Nal, D-Pal, D-APhe or D-HPhe; and Z is $GlyNH_2$ or a group —$NHC_2H_5$;

or a pharmaceutically acceptable salt thereof.

11. The peptide according to claim 10 wherein HAA is Npg which is unsubstituted or N-alpha substituted by a ($C_1$–$C_4$)alkyl group; or a pharmaceutically acceptable salt thereof.

12. The peptide according to claim 11 wherein HAA is Npg which is N-alpha-methylated; or a pharmaceutically acceptable salt thereof.

13. The peptide according to claim 10 wherein A3 is Trp; or a pharmaceutically acceptable salt thereof.

14. The peptide according to claim 13 wherein HAA is Npg which is unsubstituted or N-alpha substituted by a ($C_1$–$C_4$)alkyl group; or a pharmaceutically acceptable salt thereof.

15. The peptide according to claim 14 wherein HAA is Npg which is N-alpha-methylated; or a pharmaceutically acceptable salt thereof.

16. The peptide according to claim 2, in which:

A1 is pGlu or N-Ac-D-Nal;

A2 is an aromatic D-amino acid;

A6 is Gly, D-Pro, D-Ser, D-Thr, D-Cys, D-Met, D-Pen, D-(S-Me)Pen, D-(S-Et)Pen, D-Ser(OBu$^t$), D-Asp (OBu$^t$), D-Glu(O-Bu$^t$), D-Thr(O-Bu$^t$), D-Cys(O-Bu$^t$), an aliphatic D-amino acid with a ($C_1$–$C_8$)alkyl or a ($C_3$–$C_6$)cycloalkyl side chain, an aromatic D-amino acid, or a basic L- or D-amino acid; and Z is $GlyNH_2$ or $D\text{-}AlaNH_2$;

or a pharmaceutically acceptable salt thereof.

17. The peptide according to claim 16, which is selected from the group consisting of

[N-Ac-D-$Nal^1$-D-$pClPhe^2$-D-$Pal^3$-$NicLys^5$-$DNicLys^6$-$Npg^7$-$Iprlys^8$-D-$Ala^{10}$]LHRH, as depicted by SEQ ID NO:23;

[N-Ac-D-$Nal^1$-D-$pClPhe^2$-D-$Pal^3$-$DCit^6$-$Npg^7$-D-$Ala^{10}$] LHRH, as depicted by SEQ ID NO:24;

[N-Ac-D-$Nal^1$-D-$pClPhe^2$-D-$Pal^3$-$DCit^6$-$Npg^7$-$IprLys^8$-D-$Ala^{10}$]LHRH, as depicted by SEQ ID NO:25;

[N-Ac-D-$Nal^1$-D-$pClPhe^2$-D-$Pal^3$-$DHCit^6$-$Npg^7$-$IprLys^8$-D-$Ala^{10}$]LHRH, as depicted by SEQ ID NO:26; and

[N-Ac-D-$Nal^1$-D-$pClPhe^2$-D-$Pal^3$-DHCit6-Npg7-D-$Ala^{10}$] LHRH, as depicted by SEQ ID NO:27.

18. The peptide according to claim 16 wherein HAA is Npg which is unsubstituted or N-alpha substituted by a ($C_1$–$C_4$)alkyl group; or a pharmaceutically acceptable salt thereof.

19. The peptide according to claim 18 wherein HAA is Npg which is N-alpha-methylated; or a pharmaceutically acceptable salt thereof.

20. The peptide according to claim 16, in which:

A1 is N-Ac-D-Nal;

A2 is D-pClPhe;

A3 is D-Pal;

A4 is Ser;

A6 is Gly or a basic L- or D-amino acid; and

Z is D-$AlaNH_2$;

or a pharmaceutically acceptable salt thereof.

21. The peptide according to claim 20 wherein HAA is Npg which is unsubstituted or N-alpha substituted by a ($C_1$–$C_4$)alkyl group; or a pharmaceutically acceptable salt thereof.

22. The peptide according to claim 21 wherein HAA is Npg which is N-alpha-methylated; or a pharmaceutically acceptable salt thereof.

* * * * *